US010583146B2

(12) United States Patent
Skrtic et al.

(10) Patent No.: US 10,583,146 B2
(45) Date of Patent: *Mar. 10, 2020

(54) PHARMACEUTICAL COMPOSITIONS FOR GLUCOCORTICOID REPLACEMENT THERAPY

(71) Applicant: Shire ViroPharma Incorporated, Lexington, MA (US)

(72) Inventors: Stanko Skrtic, Mölndal (SE); Jörgen Johnsson, Helsingborg (SE); Hans Lennernäs, Uppsala (SE); Thomas Hedner, Gällstad (SE); Gudmundur Johannsson, Halmstad (SE)

(73) Assignee: SHIRE VIROPHARMA INCORPORATED, Lexington, MA (US)

( * ) Notice: Subject to any disclaimer, the term of this patent is extended or adjusted under 35 U.S.C. 154(b) by 605 days.

This patent is subject to a terminal disclaimer.

(21) Appl. No.: 14/255,332

(22) Filed: Apr. 17, 2014

(65) Prior Publication Data

US 2014/0242167 A1 Aug. 28, 2014

Related U.S. Application Data

(63) Continuation of application No. 13/722,013, filed on Dec. 20, 2012, now abandoned, which is a continuation of application No. 11/587,514, filed as application No. PCT/EP2005/000440 on Apr. 21, 2005, now Pat. No. 8,425,937.

(60) Provisional application No. 60/564,205, filed on Apr. 22, 2004.

(30) Foreign Application Priority Data

Apr. 22, 2004 (SE) ..................... 0401031

(51) Int. Cl.
  *A61K 9/28* (2006.01)
  *A61K 31/573* (2006.01)
  *A61K 9/24* (2006.01)
  *A61K 9/20* (2006.01)

(52) U.S. Cl.
  CPC ............ *A61K 31/573* (2013.01); *A61K 9/209* (2013.01); *A61K 9/28* (2013.01); *A61K 9/2031* (2013.01)

(58) Field of Classification Search
  CPC ........ A61K 31/573; A61K 9/209; A61K 9/28; A61K 9/2031
  USPC ...................................................... 424/468
  See application file for complete search history.

(56) References Cited

U.S. PATENT DOCUMENTS

| 6,143,353 A | 11/2000 | Oshlack et al. |
| 6,156,743 A | 12/2000 | Whitcomb |
| 6,500,459 B1 | 12/2002 | Chhabra et al. |
| 6,602,521 B1 | 8/2003 | Ting et al. |
| 6,682,759 B2 | 1/2004 | Lim et al. |
| 8,263,582 B2 | 9/2012 | Stergis et al. |
| 2002/0099361 A1 | 7/2002 | Faour |
| 2003/0055028 A1 | 3/2003 | Stergiopoulos et al. |
| 2003/0235617 A1 | 12/2003 | Martino et al. |
| 2012/0183610 A1 | 7/2012 | Lennernas et al. |

FOREIGN PATENT DOCUMENTS

| EP | 0745382 | 12/1996 |
| EP | 0665744 B1 | 12/1997 |
| EP | 1 382 330 A1 | 1/2004 |
| FR | 2209585 | 7/1974 |
| GB | 1458676 | 12/1976 |
| WO | 92/11001 | 7/1992 |
| WO | 96/25922 | 8/1996 |
| WO | 98/48782 | 11/1998 |
| WO | 02/072033 | 9/2002 |
| WO | 03015793 A1 | 2/2003 |
| WO | 2005065692 | 7/2005 |
| WO | WO-2005/102287 A2 | 11/2005 |
| WO | 2008065386 A1 | 6/2008 |
| WO | 2010115615 A1 | 10/2010 |
| WO | 2011144327 A1 | 11/2011 |

OTHER PUBLICATIONS

Bensing, Sophie et al., "Increased death risk and altered cancer incidence pattern in patients with isolated or combined autoimmune primary adrenocortical insufficiency", Clinical Endocrinology, 69: 697-704 (2008).
Bergthorsdottir, Ragnhildur et al., "Premature Mortality in Patients with Addison's Disease: A Population-Based Study", The Journal of Clinical Endocrinology & Metabolism, 91(12): 4849-4853 (2006).
Dallman, MF et al., "Bottomed out: metabolic significance of the circadian trough in glucocorticoid concentrations", International Journal of Obesity, 24: S40-S46 (2000).
Dallman, Mary F., "Minireview: Glucocorticoids—Food Intake, Abdominal Obesity, and Wealthy Nations in 2004", Endocrinology, 145(6): 2633-2638 (2004).

(Continued)

*Primary Examiner* — Adam C Milligan
(74) *Attorney, Agent, or Firm* — Choate Hall & Stewart LLP; Charles E. Lyon; Tracy L. Vrablik

(57) ABSTRACT

The invention relates to glucocorticoid replacement therapy and provides pharmaceutical compositions and kits designed to deliver one or more glucocorticoids to a subject in need thereon in a manner that results in serum levels of the glucocorticoid that essentially mimic that of a healthy subject for a clinically relevant period of time. The pharmaceutical compositions and kits are prepared in such a way that a first part of one or more glucocorticoids is substantially immediately released and a second part of one or more glucocorticoids is released over an extended period of time of at least about 8 hours. The invention also relates to a method for treating diseases requiring glucocorticoid treatment such as in subjects having a glucocorticoid deficiency disorder.

23 Claims, 20 Drawing Sheets

(56) References Cited

OTHER PUBLICATIONS

Figure 1:
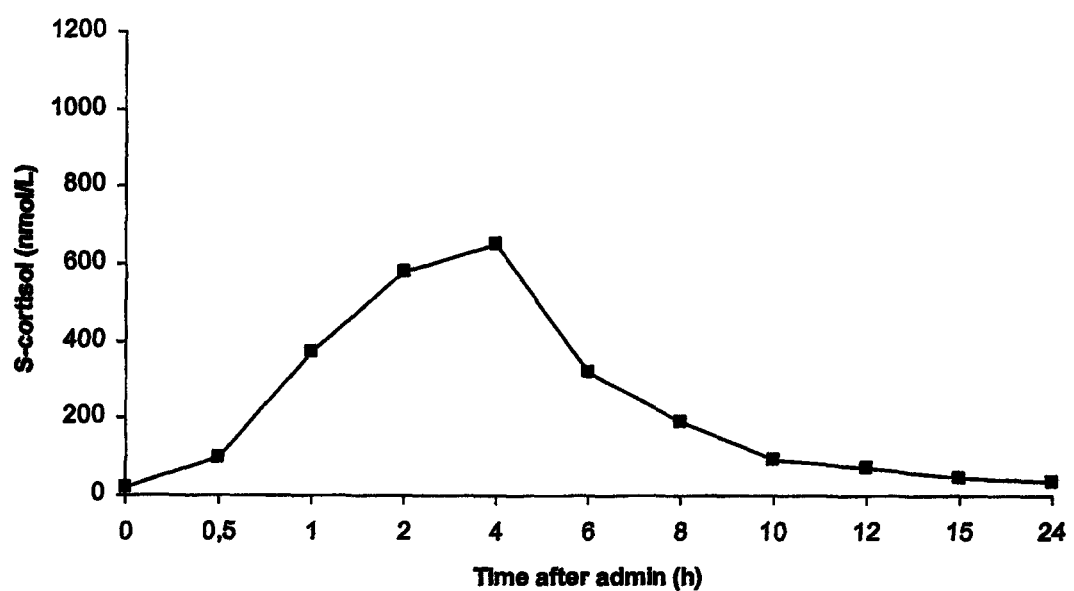

Danilowicz, Karina et al., "Correction of cortisol overreplacement ameliorates morbidites in patients with hypopituitarism: a pilot study", Pituitary, 11: 279-285 (2008).
Debono, Miguel et al., "Inadequacies of glucocorticoid replacement and improvements by physiological circadian therapy", European Journal of Endocrinology, 160: 719-729 (2009).
Debono, M et al., "Novel strategies for hydrocortisone replacement", Best Practice & Research Clinical Endocrinology & Metabolism, 23: 221-232 (2009).
Dunne, Fidelma et al., "Cardiovascular function and glucocorticoid replacement in patients with hypopituitarism", Clinical Endocrinology, 43: 623-629 (1995).
Esteban, Nora V. et al., "Daily Cortisol Production Rate in Man Determined by Stable Isotope Dilution/Mass Spectrometry", Journal of Clinical Endocrinology and Metabolism, 72(1): 39-45 (1991).
Filipsson, Helena et al., "The Impact of Glucocorticoid Replacement Regimens on Metabolic Outcome and Comorbidity in Hypopituitary Patients", The Journal of Clinical Endocrinology & Metabolism, 91(1): 3954-3961 (2006).
Groves, R.W., et al., "Corticosteroid replacement therapy: twice or thrice daily?", Journal of the Royal Society of Medicine, 81: 514-516 (1988).
Kraan, Gijsbert P.B., "The Daily Cortisol Production Reinvestigated in Healthy Men. The Serum and Urinary Cortisol Production Rates are not Significantly Different", Journal of Clinical Endocrinology and Metabolism, 83(4): 1247-1252 (1998).
Lovas, Kristian et al., "Continuous subcutaneous hydrocortisone infusion in Addison's disease", European Journal of Endocrinology, 157: 109-112 (2007).
Mason, A. Stuart et al., "Epidemiological and Clinical Picture of Addison's Disease", The Lancet, 744-747 (1968).
McConnell, E.M. et al., "Effects of low-dose oral hydrocortisone replacement versus short-term reproduction of physiological serum cortisol concentrations no insulin action in adult-onset hypopituitarism", Clinical Endocrinology, 56: 195-201 (2002).
Mills, James L., "Long-Term Mortality in the United States Cohort of Pituitary-Derived Growth Hormone Recipients", J. Pediatr., 144: 430-436 (2004).
Peace, K.A. et al., "The effect of treatment variables on mood and social adjustment in adult patients with pituitary disease", 46: 445-450 (1997).
Peacey, Steven R. et al., "Glucocorticoid replacement therapy: are patients over treated and does it matter?", Clinical Endocrinology, 46: 255-261 (1997).
Reynolds, Rebecca M. et al., "Assessing the HPA axis in patients with pituitary disease: a UK survey", Clinical Endocrinology, 64: 82-85 (2006).

Rosen, Thord et al., "Premature mortality due to cardiovascular disease in hypopituitarism", The Lancet, 336: 285-288 (1990).
Suliman, M. Abdulwahab et al., "The impact of different glucocorticoid replacement schedules on bone turnover and insulin sensitivity in patients with adrenal insufficiency", Clinical Endocrinology, 59: 380-387 (2003).
Tomlinson, J.W. et al., "Association between premature mortality and hypopituitarism", The Lancet, 357: 425-431 (2001).
Xu, Jian et al., "Assessment of the Impact of Dosing Time on the Pharmacokinetics/Pharmacodynamics of Prednisolone", The AAPS Journal, 10(2): 331-341 (2008).
Takasu, S et al., "Addison Disease and Adrenal Crisis", Today's Therapy, 44: 486 (2002) [English translation of relevant disclosure].
Shibata, T. et al., "Addison Disease", Clinical Nutrition, 89(4): 508-509 (1996) [English translation of relevant disclosure].
Shin-Yakuzaigaku Soron, New Generality of Pharmaceutics, 3rd ed., Teisuke Okano. Tokyo: Nankodo, 262-268 (1987) [English translation of relevant disclosure].
Bolt, H.M., "Principles of circadian and alternative therapy with corticosteroids and the influence upon pituitary-adrenal system", Allergologie, 3(4): 171-176 (1980).
Johannsson, Gudmundur et al., "Improving glucocorticoid replacement therapy using a novel modified-release hydrocortisone tablet: a pharmacokinetic study", European Journal of Endocrinology, 161: 119-130 (2009).
Chan, Sharon et al., "Replication of cortisol circadian rhythm: new advances in hydrocortisone replacement therapy", Ther. Adv. Endocrinol. Metab., 1(3): 129-138 (2010).
Lennernas, Hans et al., "Replacement therapy of oral hydrocortisone in adrenal insufficiency: the influence of gastrointestinal factors", Expert Opin. Drug Metab. Toxicol., 4(6): 749-758 (2008).
Johannsson, Gudmundur et al., "The metabolic impact of improving diurnal cortisol exposure in patients with adrenal insufficiency", Endocrine Journal, 57: S307, Mar. 2010 [Abstract].
El-Egakey, M.A., "Release Study of Some Drugs from Polymeric Matrices", Pharmazie, 29, H, 4: 286-290 (1974).
Chakraborty et al., "Mathematical Modeling of Circadian Cortisol Concentrations Using Indirect Respnose Models: Comparison of Several Methods", Journal of Pharmacokinetics and Biopharmaceuties, 27(1): 23-43 (1999).
Arit et al., "Adrenal insufficiency", The Lancet, 361: 1881-1894 (May 31, 2003).
Mah et al., "Weight-related dosing, timing and monitoring hydrocortisone replacement therapy in patients with adrenal insufficiency", Clinical Endocrinology, 61: 367-375 (2004).
Czock et al., "Pharmacokinetics and Pharmacodynamics of Systemically Administered Glucocorticoids", Clin. Pharmacokinet., 44(1): 61-98 (2005).
Sachio et al., Addison Disease and Adrenal Crisis; Today's Therapy, 2002, pp. 486-489, vol. 44.
Mallappa, A. et al., A Phase 2 Study of Chronocort, a Modified-Release Formulation of Hydrocortisone, in the Treatment of Adults With Classic Congenital Adrenal Hyperplasia, J Clin Endocrinol Metab, 100(3):1137-1145 (2015).

PHARMACEUTICAL COMPOSITIONS FOR GLUCOCORTICOID REPLACEMENT THERAPY

CROSS-REFERENCE TO RELATED APPLICATIONS

This application is a continuation of U.S. patent application Ser. No. 13/722,013, filed Dec. 20, 2012, which is a continuation of U.S. patent application Ser. No. 11/587,514, filed Sep. 13, 2007 (now U.S. Pat. No. 8,425,937), which is the U.S. National Stage of International Application No. PCT/EP2005/004400, filed Apr. 21, 2005, which claims benefit of U.S. Provisional Application No. 60/564,205, filed Apr. 22, 2004 and Swedish Patent Application No. 0401031-9, filed Apr. 22, 2004. The entire disclosure of each of the aforesaid applications is incorporated by reference in the present application.

FIELD OF THE INVENTION

The invention relates to glucocorticoid replacement therapy and provides pharmaceutical compositions and kits designed to deliver one or more glucocorticoids to a subject in need thereof in a manner that results in serum levels of the glucocorticoid that essentially mimic that of a healthy subject for a clinically relevant period of time. The pharmaceutical composition comprises one or more glucocorticoids, wherein a first part of one or more glucocorticoids is substantially immediately released and a second part of one or more glucocorticoids is released over an extended period of time of at least about 8 hours, and the amount of the one or more glucocorticoids of the first part, expressed as hydrocortisone equivalents, is in a range of from about 15 to about 50% of the total hydrocortisone equivalents. The invention also relates to a kit comprising a first and a second component, the first component designed to release one or more glucocorticoids substantially immediately and the second component is designed to release one or more glucocorticoids over an extended period of time of at least 8 hours. The invention also relates to a method for treating diseases requiring glucocorticoid treatment such as in subjects having a glucocorticoid deficiency disorder. In another aspect the invention relates to the use of a first and a second amount of one or more glucocorticoids for the preparation of a pharmaceutical composition or kit for the treatment of a glucocorticoid deficiency disorder.

BACKGROUND OF THE INVENTION

Glucocorticoids are important steroids for intermediary metabolism, immune, musculoskeletal, connective tissue and brain function. Their importance is plainly evident in patients having glucocorticoid deficiency. Prior to the availability of replacement therapy their one-year survival rate was less than 20%. The production and secretion of the most important glucocorticoid, cortisol, is governed by a complex and highly efficient system that includes the hypothalamus, pituitary and the adrenal glands i.e. hypothalamic-pituitary-adrenal axis. Cortisol secretion is regulated by the suprachiasmatic nucleus of the hypothalamus into a circadian release rhythm. The timing is synchronized with the solar day by dark-light shifts, which normally reflect the habitual sleep-wake pattern. Therefore in healthy persons, the cortisol secretion has a 24-hour circadian pattern with peak serum levels in the early morning, 3-6 hours after onset of sleep, and nadir levels around midnight. Physical and psychological stressors also activate cortisol secretion. Under stress conditions such as surgery, fever, physical activity, or mental stress, serum cortisol concentration is increased by the release of cortico-releasing hormone (CRH) from the hypothalamus, which stimulates synthesis and secretion of adrenocorticotropin (ACTH) in the pituitary, which makes the adrenal cortex respond with increased production and secretion of cortisol. The estimated number of secretory bursts of ACTH is 40 per 24 h. Approximately 15 min after each burst of ACTH there is a surge of cortisol released into the circulation.

Glucocorticoid deficiency has a variety of causes. The incidence of each individual disorder associated with glucocorticoid deficiency is low. These disorders, however, often occur in children and young adults, and individuals suffering from such conditions will have to depend on substitution therapy for the rest of their lives. The prevalence of these chronic disorders is therefore significant. The substitution therapy that can be provided today may be regarded as unphysiological in terms of the plasma concentration profile and the release profile of the glucocorticoids from the preparations used.

The onset of adrenocortical insufficiency may vary from insidious to an acute life-threatening situation with severe salt and water deficit, which leads to shock and death if not treated adequately. Frequently reported symptoms associated with more insidious adrenocortical insufficiency are asthenia, weakness, lethargy, easy fatigability, nervousness, irritability, apathy, dizziness, headache, myalgia, anorexia, weight loss, nausea, vomiting, and diarrhea. A recent review by Arit et al. (Lancet (2003) 361, 1881-1893) inter alia describes conditions leading to adrenal insufficiency and is hereby incorporated by reference. Three general types of adrenocortical insufficiency can be discerned. Primary adrenocortical insufficiency is usually referred to as Addison's disease. In this disorder, the adrenal cortex is affected meaning that the function of the three hormone systems produced in the adrenal cortex is impaired. The consequence of Addison's disease is therefore insufficient production and secretion of cortisol, adrenal androgens and mineralocorticoids (aldosterone).

Secondary or central adrenocortical insufficiency is mainly caused by tumours in the hypothalamic-pituitary area. The problem and the treatment considerations of secondary glucocorticoid deficiency are, however, similar to those in patients with primary adrenal failure.

Tertiary adrenal insufficiency is probably the most common cause of glucocorticoid deficiency. It is a result of long term, high dose glucocorticoid therapy as a part of treatment in patients with pulmonary diseases, autoimmune and inflammatory diseases and in the treatment of various malignancies, which results in the suppression of endogenous secretion of adrenal glucocorticoids. Tertiary adrenal insufficiency may last from a few weeks to a year.

In most cases of primary and secondary adrenal insufficiency replacement therapy with glucocorticoids is a life long treatment. The aim of glucocorticoid replacement therapy is to mimic the circadian serum cortisol profile, respond to the increased cortisol need during physical and psychological stimuli and obtain normal well-being, metabolism and long-term outcome. Both during childhood and adulthood, under-treatment can lead to malaise, postural hypotension, poor response to stress and electrolyte disturbances and even acute adrenal crisis. In childhood, an appropriate replacement dose of glucocorticoids is crucial to avoid growth suppression and reduced final height potential that are associated with glucocorticoid excess. In adults, excessive glucocorticoid replacement may induce glucose intolerance, abdominal obesity, hyper-tension, protein catabolism and osteoporosis.

Currently, the usual replacement regimen for cortisol in adults consists of 15-30 mg of hydrocortisone administered in two or three doses over a day. Synthetic glucocorticoids, such as dexamethasone or prednisolone of a longer duration are also used in replacement therapy. These synthetic compounds are, however, more potent that hydrocortisone. Their use thus increases the risk of over-treatment and adverse effects.

The estimated daily cortisol production rate in normal subjects varies between 4-15 mg/m$^2$ per day or, according to more recent studies between 9 and 11 mg/m$^2$ per day. In order to describe the 24-hour variation in serum cortisol levels adequately, one study divided the day into four phases. Phase 1 is a 6-hours period of minimal secretory activity 4 h before and 2 h after onset of sleep. Phase 2 refers to the $3^{rd}$ to $5^{th}$ hours of sleep when there is a preliminary nocturnal secretory episode. Phase 3 is a 4-hour main secretory phase during the last 3 h of sleep and the first hour after wakening. Phase 4 is an 11-hour phase of intermittent secretory activity when there is a slow decline in serum levels of cortisol.

In a study by Mah et al. (Clinical Endocrinology (2004) 61, 367-375) the circadian rhythm of serum cortisol of normal subjects is described. Peak levels of about 400-800 mmol/l, about 150-300 mmol/l and about 150 mmol/l are observed at about 6 am, 2 pm and 9 pm, respectively, and the lowest level is about midnight. In this study it is observed that the endogenous cortisol levels reach their highest levels within 30 minutes after wake-up. In order to mimic the circadian rhythm, Mah et al. recommend a thrice-daily treatment regimen of hydrocortisone, the first dose taken in the fasted state and delaying the breakfast 1-3 hours and the other two doses taken 15-60 min before food. A trice-daily regimen is also recommended in a recent review by Czock et al. (Clin. Pharmacokinet (2005) 44, 61-98) due to the short half-life of hydrocortisone, and for prednisolone a twice-daily regimen is preferred over a once-daily regimen.

A twice-daily administration of hydrocortisone with two-thirds of the total dose administered in the morning and the remainder in the afternoon (4-6 pm), results in a very low serum level of cortisol in late afternoon (3-6 pm) and late night/early morning (3-8 am). In this administration regime peak serum cortisol levels are found to surpass those observed in healthy subjects. Furthermore, patients on long term glucocorticoid replacement therapy more frequently have a low bone mineral density and an abnormal glucose tolerance.

Another problem of the need for two or three administrations per day under current treatment is that it results in non-compliance, either missing a dose or missing the timing of a dose, which leads to similar sub-optimal outcomes, especially over long periods of time. The present inventors address this problem by the once-daily aspect of the invention.

WO 02/072033 (Penwest Pharmaceuticals Co) describes a chronotherapeutic dosage form containing glucocorticosteroid. The dosage form is designed to release the glucocorticosteroid after a lag time of 2-18 hours after administration. The dosage form is intended to be administered before sleep and to start the release during sleep in order to provide the required serum level at wake-up time. However, due to large variations within and between individuals of the transit time in the various parts of the gastrointestinal tract, it is contemplated that it is difficult to reach the desired cortisol serum level at the desired point in time before wakening up.

Accordingly, there is a need of improved therapies for the treatment of a glucocorticoid deficiency disorder, which is more adapted to mimic the circadian cortisol serum profile. To this end, there is a need for an improved pharmaceutical composition or kit that enables a faster on-set of action and a longer-lasting effect compared to commercially available compositions. Furthermore, such kits or compositions may lead to better patient compliance as the dose frequency can be reduced to once daily.

DETAILED DESCRIPTION OF THE INVENTION

The present invention provides such glucocorticoid-containing pharmaceutical compositions and kits that are designed to release a first part of the glucocorticoid relatively fast in order to enable a fast on-set of action and to release a second part of the glucocorticoid in an extended manner in order to obtain a prolonged and sustained effect of the glucocorticoid. Preferably, the compositions and kits are designed for once daily administration.

Accordingly, in a first aspect the present invention provides a pharmaceutical composition comprising one or more glucocorticoids, wherein a first part of one or more glucocorticoids is substantially immediately released and a second part of one or more glucocorticoids is released over an extended period of time of at least about 8 hours, the amount of the one or more glucocorticoids of the first part, expressed as hydrocortisone equivalents, being in a range of from about 15 to about 50% of the total hydrocortisone equivalents in the composition and determined as the amount released 1 hour after start of testing of the composition in an in vitro dissolution test according to USP employing USP Dissolution Apparatus No. 2 (paddle), 50 rpm and simulated intestinal fluid without enzymes as dissolution medium, wherein at least about 50% of the hydrocortisone equivalents of the first part are released within the first 45 min of the dissolution test.

A pharmaceutical composition according to the invention is suitably designed as a single composition intended for oral administration once daily. Such a composition is convenient for the patient to take and is therefore a preferred aspect. However, within the scope of the present invention a composition of the invention may also be a dual composition, i.e. including two different pharmaceutical forms, e.g. an extended release tablet to be ingested together with an immediate release oral pharmaceutical formulation of a glucocorticoid (or other suitable combinations). Such dual compositions are normally provided in a single package such as a kit. Accordingly, the invention also provides a kit comprising i) a first component comprising one or more glucocorticoids, the first component being designed for substantially immediately release of the one or more glucocorticoids, ii) a second component comprising one or more glucocorticoids, the second component being designed for extended release of the one or more glucocorticoids, wherein at least about 50% of the one or more glucocorticoids of the first component are released within the first 45 min of a dissolution test employing USP Dissolution Apparatus No. 2 (paddle), 50 rpm and simulated intestinal fluid without enzymes as dissolution medium.

In a third aspect, the invention relates to a method for treating a subject suffering from a glucocorticoid deficiency disorder, the method comprises administering to the subject a first effective amount of one or more glucocorticoids that leads to a fast rise in the glucocorticoid serum level and a second effective amount of one or more glucocorticoids that leads to an effective serum concentration of the one or more glucocorticoids during an extended period of time of at least about 8 hours.

In a fourth aspect, the invention relates to the use of a first and a second amount of one or more glucocorticoids for the preparation of a pharmaceutical composition or kit as described herein for the treatment of a glucocorticoid deficiency disorder.

In the present context the term "extended release" is intended to include all types of release which differ from the release obtained from plain tablets and that provide a release during 8 hours or more, which is a longer period of time than that obtained from plain tablets. Thus, the term includes so-called "controlled release", "modified release", "sustained release", "pulsed release", "prolonged release", "slow release", "chrono-optimized release" as well as the term "pH dependant release".

In the same manner, the term "immediate release" is intended to include all types of release which differ from the release obtained from plain tables and provide a release, which is faster than that obtained from plain tablets.

By using one or more glucocorticoids for immediate release and one or more glucocorticoids for extended release it is contemplated that it is possible to lower the daily dosage range required to obtain a suitable therapeutic effect taking into consideration the general release profile differences in individual patients their sensitivity to the drug, and their body weights. Thus, for an average adult person, whose endogenous cortisol excretion is at a very low or zero level, the total daily dose of hydrocortisone in the range of 15-30 mg or equivalent doses of other glucocorticoids can be administered once a day in order to essentially mimic the endogenous release profile. In the present context, the term "essentially mimic" is intended to denote that the serum profile obtained in a time period corresponding to from about 0.5-1 to about 6.5-7 hours after administration of the composition or a kit according to the invention substantially imitates or resembles the shape of the serum profile of cortisol of a healthy subject in the morning from 6 am to noon. In the case that the first and the second parts (or components in the case of a kit) of the one or more glucocorticoids are taken sequentially, the time period runs from administration of the first part.

The pharmaceutical composition or kit of the invention should provide intestinal drug absorption for about 12-18 hours after dosing.

In the following is given a detailed description of the invention relating to pharmaceutical composition. However, all details and particulars disclosed under this aspect of the invention apply mutatis mutandis to the other aspects of the invention. Especially, it should be noted that disclosure relating to the first and/or the second parts of a composition according to the invention also applies for a first and second component of a kit according to the invention.

Pharmaceutical Compositions—First and Second Parts

As mentioned above, the invention relates to glucocorticoid-containing pharmaceutical compositions. A first part of the composition releases the glucocorticoid relatively quickly. For some kinds of pharmaceutical compositions it may be easy to define which part is the immediate release part (e.g. in the case of capsules containing differently colored pellets, one color for immediate release and another for extended release or in the case of a layered tablet, where the immediate release layer is on top of the extended release layer). During manufacturing of the composition it may also be relatively easy to subject the individual parts (i.e. the immediate release part and the extended release part) e.g. to in vitro dissolution test in order to evaluate the release behavior. However, with a final composition as the starting point it may in most case be difficult to define which part of the composition that is the immediate release part and which is the extended release part. Accordingly, in the present context the "immediate release part" of a composition according to the present invention is defined as the amount—expressed as hydrocortisone equivalents—released 1 hour after start of testing of the composition in an in vitro dissolution test according to USP employing USP Dissolution Apparatus No. 2 (paddle), 50 rpm and simulated intestinal fluid without enzymes as dissolution medium. In contrast to known compositions without both an immediate release and extended release part i) the immediate release part contains from about 15 to about 50% of the total hydrocortisone equivalents contained in the composition, ii) at least about 50% of the hydrocortisone equivalents of the first part are released within the first 45 min of the dissolution test, and iii) the second part releases the glucocorticoid over an extended period of time of at least about 8 hours.

The term "hydrocortisone equivalents" is used herein to define the amount in mg of a specific glucocorticoid that corresponds to 1 mg of hydrocortisone for the purpose of systemic glucocorticoid therapy as generally understood by medical practitioners. The term is based on the fact that the individual glucocorticoids have different potencies and in order to achieve a desired therapeutic effect different doses of the individual glucocorticoids are required. Equivalent doses of the glucocorticoids can be calculated based on the following table.

| Glucocorticoid | Equivalent amount (mg) | Hydrocortisone equivalent (1 mg of the glucocorticoid corresponds to the listed amount in mg of hydrocortisone) |
| --- | --- | --- |
| Cortisone acetate | 25 | 0.8 |
| Hydrocortisone | 20 | 1 |
| Prednisolone | 5 | 4 |
| Prednisone | 5 | 4 |
| Methylprednisolone | 4 | 5 |
| Triamcinolone | 4 | 5 |
| Paramethasone | 2 | 10 |
| Betamethasone | 0.75 | 26.66 |
| Dexamethasone | 0.75 | 26.66 |
| Fludrocortisone | 0.05 | 400 |

Accordingly, if the first part of the composition contains 1.5 mg betamethasone (corresponding to 40 mg hydrocortisone) and the second part of the composition contains 40 mg hydrocortisone, the total amount of hydrocortisone equivalents in the composition corresponds to 80 mg hydrocortisone. Accordingly, the first part contains 50% of the total hydrocortisone equivalents of the composition. Assuming that the total amount of the glucocorticoid in the first part is released within 1 hour in the above-mentioned dissolution test, the requirement with respect to release of the glucocorticoid from the first part within the first 45 min is that at least 25% of the total hydrocortisone equivalents are released.

Release of First Part

Specific embodiments of the first part of the composition fulfil one or more of the requirements given in the following table. In general, it is preferred that the requirement stated within 30 min after start of the dissolution test is fulfilled. In preferred embodiments, at least 70% or at least 80% of the hydrocortisone equivalents contained in the first part are released within the first 30 min of the dissolution test.

| time after start of the dissolution test | % hydrocortisone equivalents released (based on the content in the first part) |
| --- | --- |
| within 45 min | at least about 50% such as, e.g., at least about 60%, preferably at least about 70%, at least about 80% or at least about 90% |
| preferably within 30 min | at least about 50% such as, e.g., at least about 60%, preferably at least about 70%, at least about 80% or at least about 90% |
| within 20 min | at least about 50% such as, e.g., at least about 60%, at least about 70%, at least about 80% or at least about 90% |
| within 15 min | at least about 50% |

In order to be able to obtain a relatively high serum level of the glucocorticoids relatively fast after administration of a composition according to the invention, the amount of one or more glucocorticoids of the immediate release part, expressed as hydrocortisone equivalents, is in a range of from about 15 to about 50% such as, e.g., from about 20 to about 40% or from about 25 to about 35% of the total hydrocortisone equivalents in the composition.

The second part of the composition is designed to release the one or more glucocorticoids in an extended manner, i.e. the release takes place during a time period of at least about 8 hours.

In specific embodiments, the second part of one or more glucocorticoids is released over an extended period of time of at least about 10 hours. Depending on the specific formulation technique employed to prepare a composition according to the invention different release patterns can be achieved and in vivo—in vitro correlation may differ from one formulation technique to another. Accordingly, there may be situations where the in vitro release lasts for a much longer period of time without changing the in vivo behavior. Accordingly, in specific embodiments the second part of one or more glucocorticoids may be released over an extended period of time of at least about 12 hours such as, e.g. at least about 15 hours or at least about 20 hours. Moreover, as long a time period as 24 hours may be of relevance in the present context.

The release mentioned above may be measured in vivo by a suitable method. Such methods are currently under development and have attracted a lot of interest. However, in general an in vitro method is preferred such as that already described herein, Combined Release With respect to the release of the one or more glucocorticoids, specific embodiments of the composition fulfil one or more of the requirements given in the following table. In general, it is preferred that at least 80% or at least 90% of the hydrocortisone equivalents contained in composition are released within the first 24 hours of the dissolution test. In general the requirements described in the following table apply.

| time after start of the dissolution test | % hydrocortisone equivalents released (based on total content in the composition) |
| --- | --- |
| within 24 hours | at least about 80% |
| within 22 hours | at least about 80% |
| within 20 hours | at least about 80% |
| within 10 hours | at least about 50% |

However, as discussed above, there are situations where i) the release of the second part is much faster, ii) the one or more glucocorticoids is released within about 15 or 14 hours, and/or iii) the amount of the one or more glucocorticoids in the first part of the composition is relatively high. In such situations, one or more of the following requirements may apply.

| time after start of the dissolution test | % hydrocortisone equivalents released (based on total content in the composition) |
| --- | --- |
| within 8 hours | at least about 50% |
| within 6 hours | at least about 50% |
| within 5 hours | at least about 50% |

FIGS. 15-18 show different release patterns that are within the scope of the present invention.

Release of Second Part

The release of the second part of the one or more glucocorticoids normally starts upon administration. However, there may be situations where a certain lag time is obtained, e.g. if the second part of the composition is in the form of enteric coated tablets or pellets. With respect to the release, specific embodiments fulfil one or more of the requirements are given in the following table.

| time after start of the dissolution test | % hydrocortisone equivalents released per hour (based on the content in the second part | % hydrocortisone equivalents released per hour (based on the total content of the composition) |
| --- | --- | --- |
| from about 1 to about 8 hours | from about 3 to about 15% such as, e.g., from about 3 to about 10% | from about 1.5 to about 15% such as, e.g., from about 3 to about 15% |
| from about 1 to about 10 hours | from about 3 to about 15% such as, e.g., from about 3 to about 10% | from about 1.5 to about 15% such as, e.g., from about 3 to about 15% |
| from about 1 to about 12 hours | from about 3 to about 15% such as, e.g., from about 3 to about 10% | from about 1.5 to about 15% such as, e.g., from about 3 to about 15% |

In a specific embodiment
i) from about 3 to about 15% of the hydrocortisone equivalents contained in the second part are released per hour during a time period of from 1 to about 6 hours,
ii) from about 3 to about 10% of the hydrocortisone equivalents contained in the second part are released per hour during a time period of from about 6 to about 10 hours, and
iii) from about 3 to about 7.5% of the hydrocortisone equivalents contained in the second part are released per hour during a time period of from about 10 to about 12 hours after start of the dissolution test as defined herein.

With respect to the extended release part in principle any pharmaceutical formulation designed for extended release may be used. It is well known that the release of the active substance from some extended release formulations (e.g. matrix tablets) may be very slow especially if the release is designed as a 24+-hour release. In such cases it may be necessary to estimate the total amount of hydrocortisone equivalents in the composition in order to determine the content of the second part. Accordingly, the amount of hydrocortisone equivalents of the second part of the composition may, if relevant, be determined as $(H_{total}-H_{first\,part})$, wherein $H_{total}$ is the total amount of hydrocortisone equivalents released within 24 hours after start of the test defined in above and $H_{first\,part}$ is the amount of hydrocortisone equivalents of the first part of the composition determined as defined herein.

Active Substance

In the present context, the term "glucocorticoid" or "glucocorticosteroid" is intended to denote a therapeutically, prophylactically and/or diagnostically active glucocorticoid or a glucocorticoid that has physiologic effect. The term is intended to include the glucocorticoid in any suitable form such as e.g. a pharmaceutically acceptable salt, complex, solvate, ester, active metabolites or prodrug thereof of in any physical form such as, e.g., in the form of crystals, amorphous or a polymorphous form or, if relevant, in any stereoisomer form including any enantiomeric or racemic form, or a combination of any of the above. The glucocorticoid may be a synthetic glucocorticoid.

The one or more glucocorticoids contained in a composition according to the invention is selected from the group consisting of hydrocortisone, cortisone, prednisolone, prednisone, methylprednisone, triamcinolone, paramethasone, betamethasone, dexamethasone and fludrocortisone including pharmaceutically acceptable esters, salts and complexes thereof.

As indicated in the sections above, the one or more glucocorticoids of the first and the second part may be the same glucocorticoid or a mixture of the same glucocorticoids. Normally, this is the case as it is easy from a manufacturing point of view in those cases where both the first and the second part are parts of the same dosage form (e.g. the first and second part are contained in a tablet and the first part is provided as a coating or as a separate layer on a core containing the second part). However, in those cases where the first and second part are not part of the same dosage form (e.g. the first part is an effervescent tablet and the second part is in the form of an extended release tablet) or in those cases where an improved therapeutic result is expected when different glucocorticoids are employed, the one or more glucocorticoids of the first and the second part are different glucocorticoids or a mixture of different glucocorticoids.

As the first part of the glucocorticoid is intended for immediate release, the release and/or absorption may take place already in the oral cavity in the case the composition is administered orally. In such cases, the glucocorticoid of choice for the first part may be not be hydrocortisone (as such) or cortisone as these two active substances have a bitter taste. However, these substances may be employed provided that a sufficient taste masking is obtained. In the paragraph relating to "Pharmaceutically acceptable excipients" taste-masking is discussed in more detail. Accordingly, the one or more glucocorticoids of the first part may have an acceptable taste, may be tasteless or may be effectively taste-masked.

Examples of the one or more glucocorticoids of the first part (as discussed above) are synthetic glucocorticoids such as, e.g., hydrocortisone 21-succinate, prednisolone, prednisone, methylprednisone, triamcinolone, paramethasone, betamethasone, dexamethasone and fludrocortisone including pharmaceutically acceptable esters, salts and complexes thereof. An especially suitable example is hydrocortisone or hydrocortisone 21-succinate or a pharmaceutically acceptable salt thereof.

With respect to the second part, any of the above-mentioned glucocorticoids may be employed. In a specific embodiment hydrocortisone is preferred.

Administration Routes—Dosages

The pharmaceutical composition of the invention may be administered by a suitable administration route. Normally the oral route is preferred due to convenience for the patient, but in the case that the first and the second part of the composition are different dosage form, the first part of the composition may suitably be designed to be administered via a mucosa in the oral cavity, the nasal cavity, the rectum, the gastrointestinal mucosa, or via pulmonary, bronchial or respiratory mucosa and epithelia.

Figure 19:
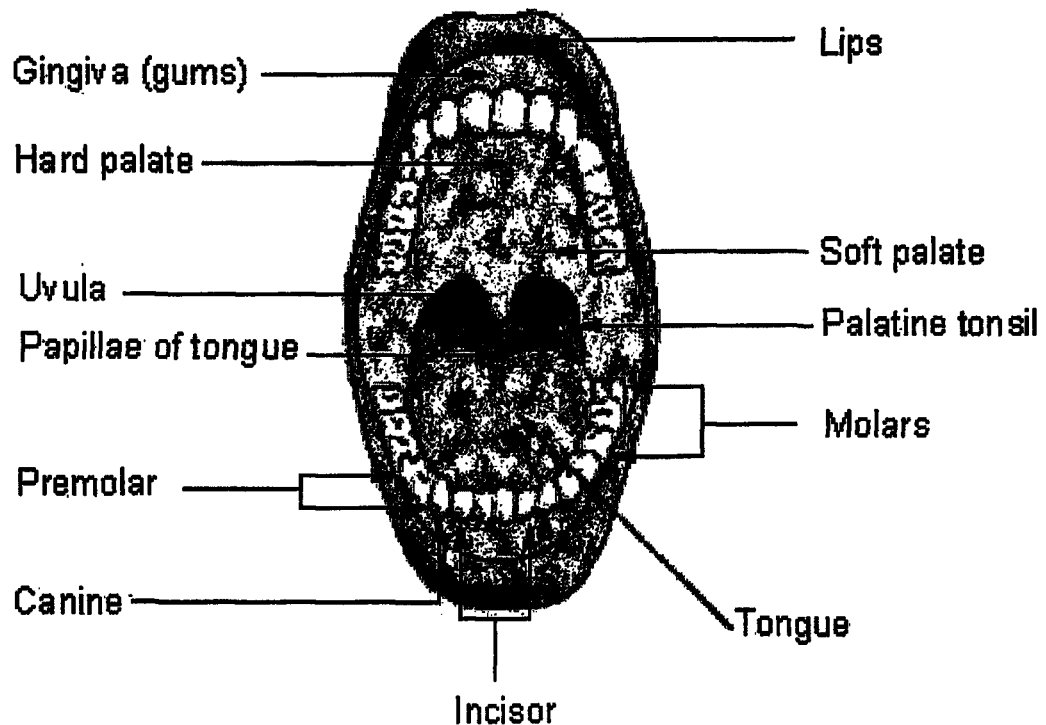
Figure 20:
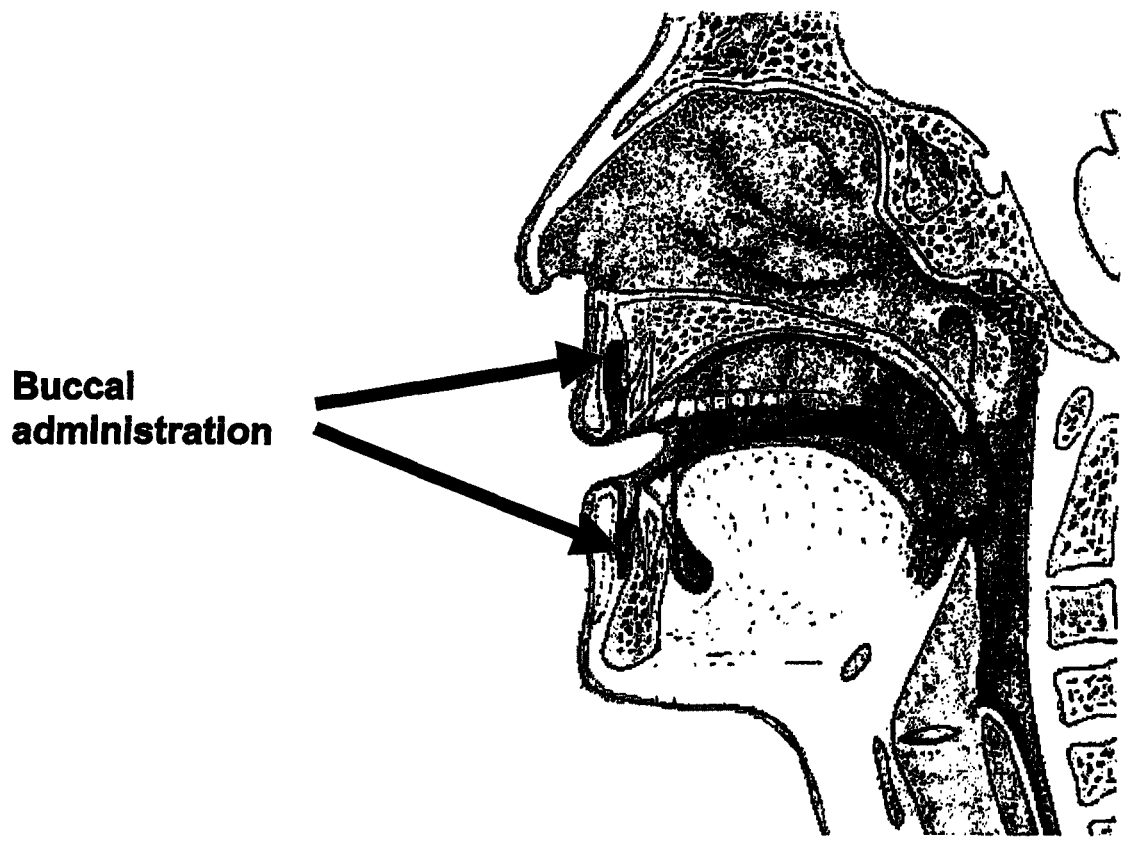

Especially for very fast on-set of action especially administration via the mucosa in the oral cavity is suitable. FIGS. 19 and 20 show sites or oral mucosal administration suitable for use. Four well-defined sites may be used, namely "buccal" administration that includes the term "labial" administration and is used for administration of a pharmaceutical composition to a mucosa between the gums (gingiva) and the inside of the cheeks;

"sublingual" administration that refers to administration of a pharmaceutical composition under the tongue;

"palatal" administration that refers to administration of a pharmaceutical composition to the hard and/or soft palate; and "gingival" administration that refers to administration of a pharmaceutical composition to the upper and/or lower gingiva.

In cases where a very fast on-set of action is required, the buccal administration route is preferred for the first part of the composition, i.e. by administration of a composition to the oral mucosa between the gums and the inside of the cheeks and thus enabling the absorption to take place from two sites, namely the gingival mucosa and the buccal mucosa.

In those cases where different dosage forms are used for the first and the second part of the composition, the final composition is normally and advantageously presented as a kit.

However, in a specific embodiment of the invention the pharmaceutical composition is a single dosage form including both the immediate release part and the extended release part. Such compositions are especially suitable for use in a long-term treatment as the composition preferably is designed to be administered once daily. However, there may be situations (e.g. due to physical activities, stress etc) where the patient may need a supplemental dose of glucocorticoid. In such situations a separate dose of the immediate release part that leads to a fast on-set can be administered to the patient.

A composition according to the present inventions aims at an administration frequency once daily. In the present context the term "once daily"/"once-a-day" is intended to mean that it is only necessary to administer the pharmaceutical composition once a day in order to obtain a suitable therapeutic and/or prophylactic response; however, any administration may comprise administration of more than one dosage unit, such as, e.g. 2-4 dosage units or different dosage units (e.g. tablets and films).

As mentioned above, a pharmaceutical composition of the invention is generally designed to be administered once daily to mimic the circadian rhythm of plasma cortisol. In order to achieve a fully physiological serum concentration time profile of cortisol in vivo a significant increase from low/undetectable serum levels of cortisol has to be achieved at approximately 4 am. This is not achievable with adequate precision with a delayed release pharmaceutical formulation administered at bedtime due to the large variation within and between individuals in gastrointestinal transit time (especially colon transit time). Hence, such a formulation with a target time for the absorption to start at 4 am will result in high variability in the onset of absorption and some patients would experience high peak value in serum earlier in the night as well as later.

Therefore the present invention aims to provide the patient with a rapid absorption in order to obtain adequate and physiological serum cortisol levels as soon as possible in the early morning. The present invention will provide a rapid absorption that will achieve clinically significant serum concentrations of cortisol (>200 nmol/L) within 30 min. This can be achieved by the present novel immediate release oral preparation or by parenteral transbuccal administration as demonstrated in the below examples. Moreover, a combination of an immediate release and an extended release can also be achieved by the use of a single composition such as exemplified herein. Accordingly, when the one or more glucocorticoids is given in a composition or kit according to the present invention, a plasma concentration-time profile is obtained that is synchronized with the biological circadian rhythms of glucocorticoid. In the present context the terms "synchronize" or "mimic" are used to denote situations where the serum level profile of glucocorticoid after administration of a composition or kit according to the present Invention has a similar shape to that of a normal healthy human subject at least for a time period corresponding to 0.5 to 6 hours after administration (i.e. if the composition or kit is administered at 6 am in the morning, the serum profile of glucocorticoid of the patient should essentially have the same shape as that of a healthy subject measured in the time period corresponding to 6.30 am to noon).

Current monitoring of glucocorticoid replacement therapy with hydrocortisone is cumbersome and not feasible. During administration b.i.d. (i.e. two times daily) two peaks will appear with low or undetectable serum levels of cortisol in-between. More frequent administration will produce a more physiological diurnal profile, but will continue to have peak and trough values. The clinical relevance of such curves is therefore not properly established. However, administration of a composition of the invention with an immediate release part (IR) and an extended release part (ER) will produce a profile that is well established in normal human physiology. This will open the possibility of tailoring the dose to the need of each individual in order to achieve a diurnal serum profile with target values as demonstrated in the table below.

In preferred embodiments a pharmaceutical composition of the present invention is designed for administration once daily in the morning. Typically, the composition is administered at wake-up time, i.e. from 4 am to noon, from 4 am to 10 am, from 4 am to 9 am, from 5 am to 8 am or from 6 am to 8 am, most typically at 6 to 8 o'clock in the morning. The composition is also designed to provide a 6-9 h "glucocorticoid-free" interval meaning low or undetectable serum levels of glucocorticoid (corresponding to <50 nmol/l cortisol) late evening and night.

In general, the dosage of the glucocorticoids present in a composition according to the invention depends inter alia on the specific drug substance, the age and condition of the patient and of the disease to be treated.

The glucocorticoids of the first and the second part of the pharmaceutical composition should each include a hydrocortisone equivalent daily dose of 5-50 mg. For the purpose of comparison, a table is given herein describing the equivalent milligram dosage of the various glucocorticoids. Thus, other forms of synthetic glucocorticoids in equivalent doses might be used. Normally, a pharmaceutical composition according to the present invention contains a total amount of hydrocortisone equivalents expressed as hydrocortisone in the composition from about 1 to about 80 mg. In specific embodiments, the total amount of hydrocortisone equivalents in the composition is from about 1 to about 75 mg such as, e.g., from about 1 to about 70 mg, from about 5 to about 60 mg, from about 5 to about 50 mg, from about 5 to about 40 mg or from about 10 to about 30 mg.

More specifically, normal daily dose ranges are given below

| | |
|---|---|
| Hydrocortisone | 1-30 mg |
| Cortisone | 1-20 mg |
| Betamethasone | 1-20 mg |
| Prednisolon | 1-10 mg |
| Dexamethasone | 0.1-2 mg |
| Fludrocortisone | 0.05-5 mg |
| Prednisone | 10-50 mg |
| Methylprednisolone | 2-20 mg |

A composition according to the invention containing a dose for once daily administration as described above is designed to provide the serum levels described in the following table (the narrow range is the preferred range, but due to individual variations serum level within the wider range is also satisfactory). The serum concentrations given below are given in terms of hydrocortisone equivalents. In the case that another glucocorticoid than hydrocortisone is used, a person skilled in the art will know how to determine suitable serum levels (cf. the guidance given herein before).

| Hours after administration | Serum concentration (nmol/L) - wide | Serum concentration (nmol/L) - narrow |
|---|---|---|
| Within the first 45 min such as, e.g. within the first 30 or 20 min | 200 or more | 200 or more |
| 2 h | 100-1000 | 400-700 |
| 6 h | 100-600 | 200-400 |
| 10 h | 50-400 | 100-300 |
| 14 h | 50-300 | 50-200 |
| 18 h | 50-100 | <50 |

Accordingly, when the glucocorticoid is given in two different parts as single dose at the same time a plasma concentration-time profile is obtained that essentially is synchronized with the biological circadian rhythms of glucocorticoid. It is preferred that the glucocorticoid is released in manner such as to provide serum levels as shown below:

| Hours after administration | Serum concentration (nmol/L) |
|---|---|
| within 30 min | 200 or more |
| 2 h | 400-700 |
| 6 h | 200-400 |
| 10 h | 100-300 |

-continued

| Hours after administration | Serum concentration (nmol/L) |
|---|---|
| 14 h | 50-200 |
| 18 h | <50 |

The pharmaceutical preparations are considered as a once-daily medication to be administered at wake-up, typically at 6 o'clock to 8 o'clock in the morning. They are thus also designed to provide a 6-9 h glucocorticoid-free interval serum levels <50 nmol/l at late evening and night, during which no extraneous glucocorticoid has to be administrated to the patient.

Pharmaceutical Dosage Forms

As it appears from the above, a composition according to the invention is designed for oral administration. In the case of a kit according to the invention, the extended release component is suitable designed for oral administration and the immediate release part may be designed for any suitable administration route, preferably via a mucosa. In preferred aspects, a composition or a kit according to the present invention is designed for oral administration, i.e. administration by oral intake or to the oral cavity.

Most suitably a pharmaceutical composition and at least the extended release component of a kit according to the present invention is in the form of a solid dosage form such as e.g. granules, beads, pellets and powders.

A composition and the individual components of a kit according to the invention is normally presented as unit dosage forms including tablets, capsules or sachets. With respect to the immediate release part or component of a kit according to the invention it may be presented as a different unit dosage form including e.g. thin film for application to the oral mucosa, solutions for application via a suitable device such as, e.g., a spray to the oral or nasal mucosa, an inhaler or powder inhaler for application via pulmonary, bronchial or respiratory mucosa and epithelia, suppositories or other suitable compositions for administration to the rectal mucosa or it may be presented as immediate release tablets including chewable tablets, suckable tablets, effervescent tablets, melt tablets, lozenges, pastilles or it may be presented in a more candy-like form.

In principle any relevant formulation technique for preparing an oral controlled release composition may be applied for the extended release part of the composition. Such compositions include e.g. diffusion-controlled drug delivery systems, osmotic pressure controlled drug delivery systems, eroding drug delivery systems etc. Thus, the composition may be in the form of a single or a multiple unit dosage form intended for use as such. In the same manner, any relevant formulation technique for preparing pharmaceutical compositions may be applied when formulating the immediate release part of a composition or a kit according to the invention. A person skilled in the art of pharmaceutical formulation techniques can find guidance in the handbook Remington's Pharmaceutical Sciences and in the Examples herein.

In the following is given a short review on general immediate and extended release formulation techniques with an aim of obtaining the type of dissolution profile described herein for the extended release part. In the compositions described below a person skilled in the art will know how to incorporate a part that gives rise to an immediate release of the one or more glucocorticoids.

Immediate Release Part of a Composition or Immediate Release Component of a Kit According to the Invention The immediate release part comprises a glucocorticoid as active substance normally together with one or more pharmaceutically acceptable excipients or carriers (herein also denoted "immediate release carrier") to provide rapid release/dissolution of the glucocorticoid in vitro and, after administration of the pharmaceutical composition to a patient, a rapid dissolution of the glucocorticoid at the administration site such as, e.g., In the oral cavity or in the gastrointestinal tract and a rapid absorption of the glucocorticoid in vivo. The one or more pharmaceutically acceptable excipients employed for the immediate release part are either inherent or they may contribute to a fast release. However, they are not intended to delay or retard the release in any manner.

The immediate release carrier comprises suitable pharmaceutical excipients and presents the glucocorticoid to the dissolution medium in vitro and in vivo in a way that provides rapid dissolution of the glucocorticoid. The immediate release part is formulated by per se known techniques such as for instance:

Finely divided/micronised particles of the glucocorticoid are thoroughly mixed with a water soluble pharmaceutically acceptable excipient(s) such as for instance lactose, mannitol or any other suitable excipient and, optionally after granulation with a suitable granulation liquid, drying and milling, optionally mixed with suitable binder(s) disintegrant(s), lubricant(s), flavouring agents, colours or other suitable agents and formed into a suitable immediate release part of the composition. The immediate release part can be formed by compression into a separate layer of a layered tablet or as the outer layer of a dry-coated tablet.

Another way to formulate the immediate release part is to first dispose a solution of the glucocorticoid onto a suitable pharmaceutical excipient(s) such as for instance lactose, mannitol or any other suitable excipient(s) and carry on as above or to first make a solid solution of the glucocorticoid in a suitable excipient such as for instance polyethylene glycol, a suitable poloxamer or any other suitable excipient and carry on as above.

The immediate release part can also be in a form of a powder mixture or a powder granulation and be mixed with an extended release part and dispensed in a capsule or a sachet. It may also be formulated into small pellets and be mixed with extended release pellets and dispensed into capsules. The mixture of the immediate release part and extended release pellets can after mixing with suitable pharmaceutical excipients to a homogeneous mixture be compressed into tablets.

In another embodiment of the invention the immediate release part may be formulated by coating an extended release tablet of the glucocorticoid or extended release pellets with a rapidly dissolving coating containing the glucocorticoid.

As mentioned hereinbefore, the immediate release part or component may also be a separate dosage unit such as, e.g., a mucoadhesive composition e.g. in the form of a thin film for buccal application or e.g. for application to the other oral mucosa.

It may also be in the form of a dosage form intended for administration to the nasal cavity such as, e.g., a nasal spray composition or it may be designed for rectal administration such as, e.g., a solid rectal composition as a suppository, or a semi-solid rectal composition as a reactiol or a fluid rectal composition as a rectal solution.

For administration to the pulmonary, bronchial or respiratory mucosa and epithelia the composition may be in the form of an inhaler or a powder inhaler.

Extended Release Part of a Composition or Extended Release Component of a Kit According to the Invention The extended release part comprises a glucocorticoid as active substance in a pharmaceutically acceptable excipient or carrier (herein also denoted "extended release carrier") to provide extended release/dissolution of the glucocorticoid in vitro and, after administration of the pharmaceutical composition to a patient, an extended dissolution of the glucocorticoid in the gastrointestinal tract and an extended absorption of the glucocorticoid in vivo.

The extended release carrier comprises suitable pharmaceutical excipients and presents the glucocorticoid to the dissolution medium in vitro and in vivo in a way that provides dissolution of the glucocorticoid at a suitable rate during a prolonged time period. The release kinetics may follow zero order, first order or a mixed first and zero order. Examples of different extended release technologies are e.g. single units (e.g. matrix tablets, coated matrix tablets, layered tablets, multilayer coated units etc) and multiple units (e.g. units having an extended release coating, units having an extended release matrix, units having an extended release compression coating, units having a multilayer coating etc.). In the following is given a description of general applicable extended release formulation techniques. In the compositions described below, a person skilled in the art will know how to incorporate an immediate release part that gives rise to a relatively fast release of the one or more glucocorticoids. As an example such a part may be incorporated in an outermost coating layer comprising the glucocorticoid for immediate release, it may be incorporated in a separate layer in a two- or multi-layered tablet or it may be incorporated in the form of pellets formulated without release-retarding agents. The extended release part is formulated by per se known techniques such as for instance:

The glucocorticoid may be embedded in a water insoluble porous matrix from which the glucocorticoid is released by diffusion through the pores. Such porous matrices can be made of insoluble plastic material, such as for instance PVC, stearic acid, paraffin or other suitable insoluble materials optionally together with suitable excipients for the formation of pores.

The glucocorticoid may also be embedded in a water insoluble matrix from which the glucocorticoid is made available for dissolution by gradual erosion of the matrix. Such eroding matrices can be made of a suitable fat or of a compact of hardly soluble or insoluble pharmaceutical excipients optionally mixed with other suitable pharmaceutical excipients.

The glucocorticoid may also be embedded in a swelling hydrophilic gel matrix from which the glucocorticoid is released by diffusion through and erosion of the matrix. Such matrices usually comprise modified cellulose material such as for instance hydroxypropyl methylcellulose in admixture with suitable pharmaceutical excipients and formulated into tablets. As examples of other suitable excipients for hydrophilic gel matrices can be mentioned by not limited to various methacrylic acid copolymers, high molecular weight polyoxyethylenes and poloxamers.

The glucocorticoid may also be formulated into a solid shape, such as for instance a tablet or pellet, with suitable dissolution properties and then coated with a release rate controlling membrane, such as for instance a membrane controlling the rate of diffusion of the active substance through the membrane or through pores in the membrane. Such membranes can for instance be made of ethyl cellulose or any other suitable membrane-forming excipient optionally containing a water soluble pore-forming substance such as for instance hydroxypropyl methylcellulose, sugar, sodium chloride or any other suitable water soluble substance and optionally plasticizers.

In specific embodiments, a pharmaceutical composition according to the invention is in the form of a tablet, wherein the one or more glucocorticoids of the first part is provided as a coating. In another specific embodiment, the one or more glucocorticoids of first and the second part are provided as pellets, granules, beads or powders.

Accordingly, the administration means can be a formulation for oral administration of both the part for immediate release and the part for extended release. For example, the composition for oral administration can be a tablet comprising the first part (immediate release) coated outside the second part (extended release). The composition for oral administration can also be a capsule comprising the first part of the composition or components of a kit according to the invention.

Pharmaceutically Acceptable Excipients

In the present context the terms "pharmaceutically acceptable excipients" are intended to denote any material, which is inert in the sense that it substantially does not have any therapeutic and/or prophylactic effect per se. Such an excipient may be added with the purpose of making it possible to obtain a pharmaceutical, cosmetic and/or foodstuff composition, which have acceptable technical properties.

Examples of suitable excipients for use in a composition or kit according to the invention include fillers, diluents, disintegrants, binders, lubricants etc. or mixture thereof. As the individual parts of a composition or kit according to the invention are used for different purposes (e.g. immediate and extended release), the choice of excipients is normally made taken such different uses into considerations. A person skilled in the art will know which kinds of pharmaceutically acceptable excipients that are suitable choices depending on the specific dosage form in question. Other pharmaceutically acceptable excipients for suitable use are e.g. acidifying agents, alkalising agents, preservatives, antioxidants, buffering agents, chelating agents, colouring agents, complexing agents, emulsifying and/or solubilizing agents, flavours and perfumes, humectants, sweetening agents, wetting agents etc.

Examples of suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel MC, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition or solid dosage form of the invention are e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

The composition or kit components according to the invention may also be coated with a film coating, an enteric coating, a modified release coating, a protective coating, an anti-adhesive coating etc.

A composition according to the invention (or part thereof) may also be coated in order to obtain suitable properties e.g. with respect to extended release of the one or more glucocorticoids. The coating may also be applied as a readily soluble film containing the one or more glucocorticoids for immediate release. The coating may also be applied in order to mask any unsuitable taste of the one or more glucocorticoids. The coating may be applied on single unit dosage forms (e.g. tablets, capsules) or it may be applied on a polydepot dosage form or on its individual units.

Suitable coating materials are e.g. methylcellulose, hydroxypropylmethylcellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, glyceryl monostearate, zein.

Plasticizers and other ingredients may be added in the coating material. The same or different active substance may also be added in the coating material.

Taste Masking

In general, it is difficult in most cases to prepare a formulation for oral mucosa or nasal administration with satisfactory safety and stability from a drug having irritating properties or capable of forming molecular aggregates, although it depends on the kind of the drug used. In the case of hydrocortisone, the base has a distinctively bitter taste and a formulation has to be taste masked in order to be applicable for repeated use.

The taste masking agent can be a menthol, a peppermint, a vanillin, or a terpene based compound. In addition, the taste masking agent can be an artificial sweetener, e.g. sorbitol, xylitol or aspartame. Taste masking can also be achieved by microencapsulation of the glucocorticoid as particles. This is for example accomplished with lecithin based compounds. The taste masking agent, is carefully mixed with the active drug in order to be present both at the surface and within the administration formulation. Taste masking can also be achieved by formation of inclusion complexes with cyclodextrins.

Typical examples of the cyclodextrin compound are alpha.-cyclodextrin, .beta.-cyclodextrin, .gamma.-cyclodextrin, hydroxypropyl .beta.-cyclodextrin, dimethyl .beta.-cyclodextrin, maltosyl .beta.-cyclodextrin and .beta.-cyclodextrin sulfate. Particularly preferred are .alpha.-cyclodextrin, .beta.-cyclodextrin and .gamma.-cyclodextrin. These cyclodextrin compounds may be used alone or in combination.

The amount of cyclodextrin compound to be used may vary with its solubility and the concentration of hydrocortisone. It is, however, desirable that the amount of cyclodextrin compound is 0.5 to 4.0 moles, preferably 2.0 to 4.0 moles, as much as the mole of hydrocortisone.

Method Aspect

A pharmaceutical composition or a kit according to the invention is suitable for use in the treatment of a subject such as a mammal including a human suffering from a glucocorticoid deficiency disorder.

Glucocorticoid deficiency disorders, to be treated according to the invention may be a primary, a secondary, or a tertiary adrenal insufficiency. Any other medical condition, in which chronic glucocorticoid administration is indicated, can also be treated according to the invention such as, e.g., systemic inflammatory diseases as inflammatory bowel disease, rheumatoid arthritis as well as other systemic rheumatoid diseases.

In a separate aspect, the invention relates to a method for treating a subject suffering from a glucocorticoid deficiency disorder, the method comprises administering to the subject a first effective amount of one or more glucocorticoids that leads to a fast rise in the glucocorticoid serum level and a second effective amount of one or more glucocorticolds that leads to an effective serum concentration of the one or more glucocorticoids during an extended period of time of at least about 8 hours.

The first and the second effective amount of the one or more glucocorticoids may be administered substantially simultaneously (i.e. within a time period of at the most 10 min, preferably within 5 min) or sequentially (with a time span of from about 10 min to about 1 hour).

By administration of the first and the second amounts of the one or more glucocorticoids, the following serum levels are obtained (expressed as hydrocortisone):

within 45 min preferably within 30 min or within 20 min after administration of the first effective amount of the one or more glucocorticoids the serum level is at least about 200 nmol/l, about 2 hours after administration of the first effective amount of the one or more glucocorticoids the serum level is in a range of from about 200 to about 1000 nmol/l preferably in a range of from about 400 to about 700 nmol/l, about 6 hours after administration of the first effective amount of the one or more glucocorticoids the serum level is in a range of from about 200 to about 600 nmol/l, preferably in a range of from about 200 to about 400 nmol/l, about 10 hours after administration of the first effective amount of the one or more glucocorticoids the serum level is in a range of from about 50 to about 400 nmol, preferably in a range of from about 100 to about 300 nmol/l, about 14 hours after administration of the first effective amount of the one or more glucocorticoids the serum level is at the most about 300 nmol/l, preferably at the most about 200 nmol/l such as in a range of from about 50 to about 200 nmol/l, about 18 hours after administration of the first effective amount of the one or more glucocorticoids the serum level is less than about 100 nmol/l, preferably less than about 50 nmol/l.

In order to obtain a serum profile that—at least during specific time periods such as, e.g., in the morning—mimics that of a healthy subject such as a human, the first and the second effective amount of the one or more glucocorticoids are administered at wake-up in the morning between about 4 am and noon such as, e.g., between 5 am and noon, between 6 am and 10 am, between 6 am and 9 am, between 6 am and 8 am.

The serum level obtained after administration of the first and the second amount of the one or more glucocorticoids mimics in a time period corresponding to from about 0.5-1 to about 6.5-7 hours after administration of the first effective amount of the one or more glucocorticoids the serum level of cortisol of a healthy subject in the morning from 6 am to noon, and normally a 3 hours substantially glucocorticoid-free serum level is obtained daily in a time period of from about 10 pm to about 6 am.

The first and the second effective amounts are administered in the form of a pharmaceutical composition or kit as defined herein. Normally, the first and the second amounts should be administered to the subject in the morning in a fasted state (i.e. no intake of food at least 4 hours before administration and at least 0.5-1 hour after administration and, if the composition of a component of the kit is in the form of a tablet, it is recommended to take the composition together with water such as, e.g., 50-300 ml of water or about 200 ml.

Use of a Composition or a Kit According to the Invention

In another separate aspect, the invention relates to the use of a first and a second amount of one or more glucocorticoids for the preparation of a pharmaceutical composition or kit as defined hereinbefore the treatment of a glucocorticoid deficiency disorder and to provide a serum level as defined herein.

LEGENDS TO FIGURES

FIG. 1 shows results from Example 6. In vivo plasma profile. Extended release tablet, 7 mm diameter, medium compression force, 20 mg hydrocortisone, oral administration. Subject has the endogenous glucocorticoid secretion suppressed by synthetic glucocorticoids.

Figure 2:
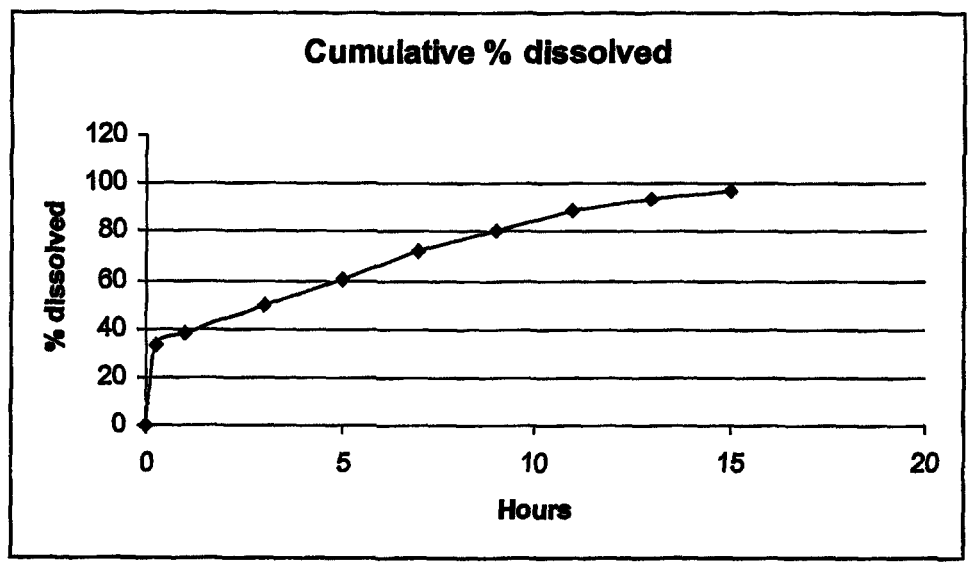

FIG. 2 shows results from Example 6. Dissolution profile of IR-ER tablet

Figure 3:
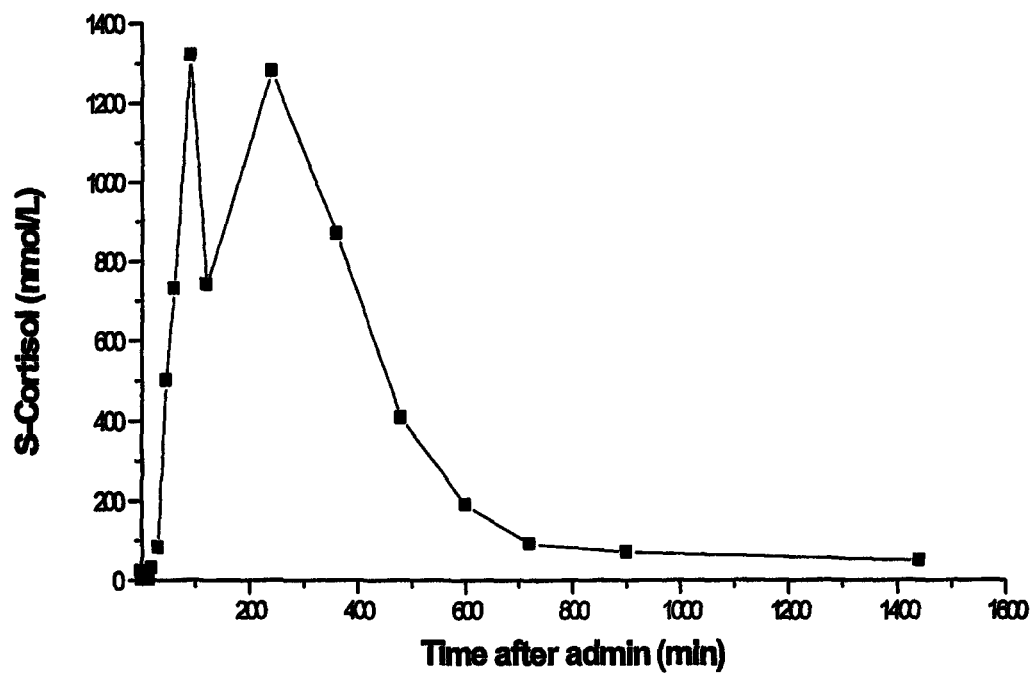

FIG. 3 shows results from Example 11. In vivo plasma profile. Extended release tablet, 7 mm diameter, medium compression force, 20 mg hydrocortisone, oral administration and mucoadhesive thin-layer film 10 mg hydrocortisone, buccal administration. Subject has the endogenous glucocorticoid secretion suppressed by synthetic glucocorticoids.

Figure 4:
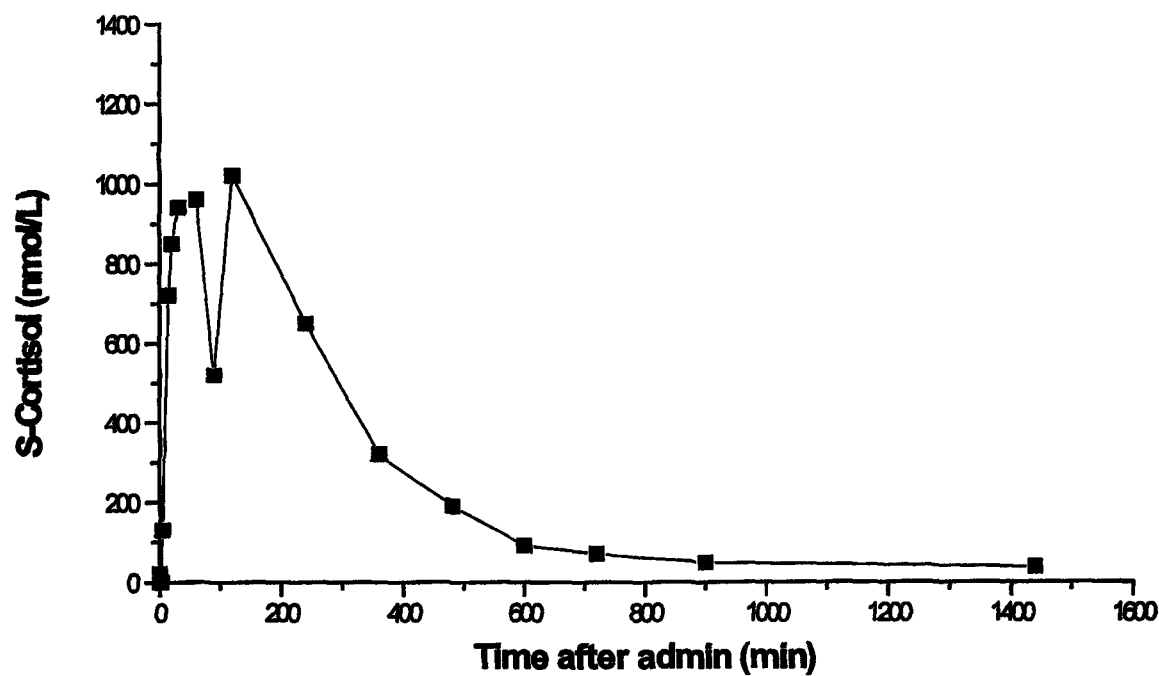
Figure 5:
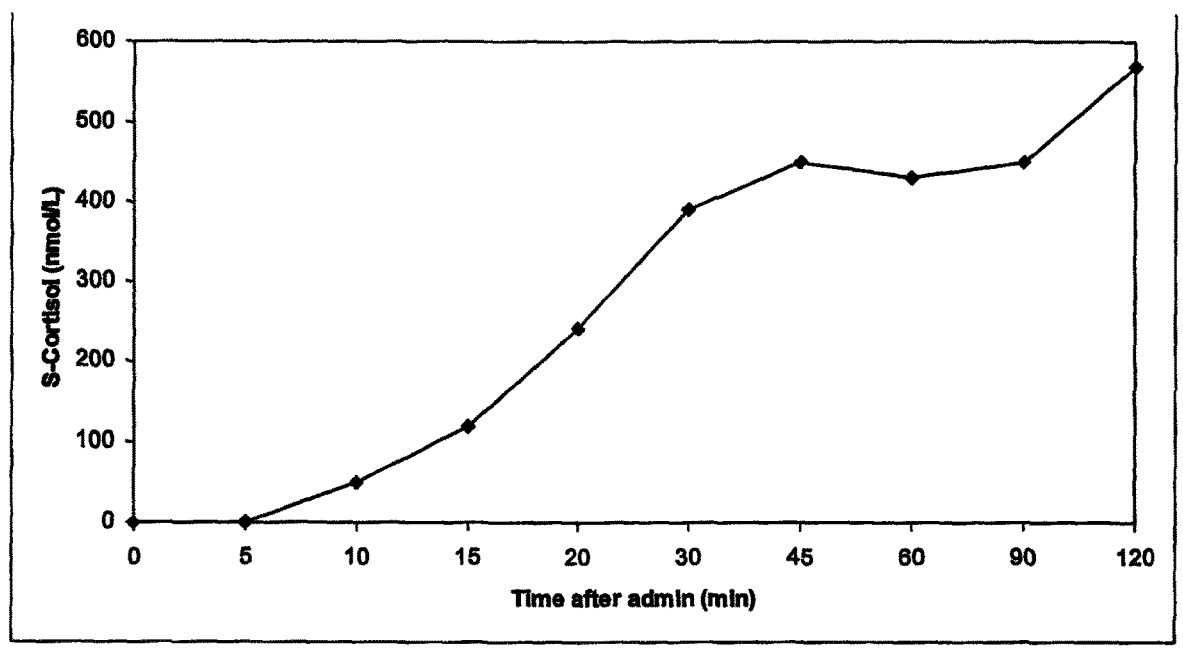
Figure 6:
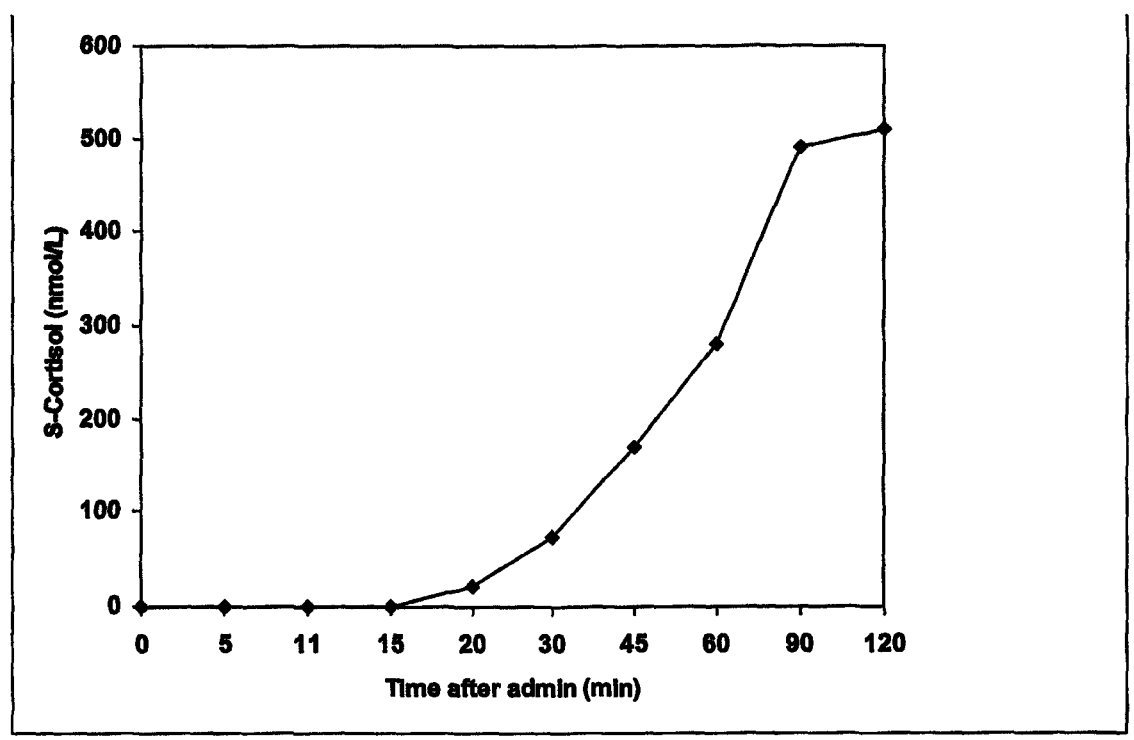
Figure 7:
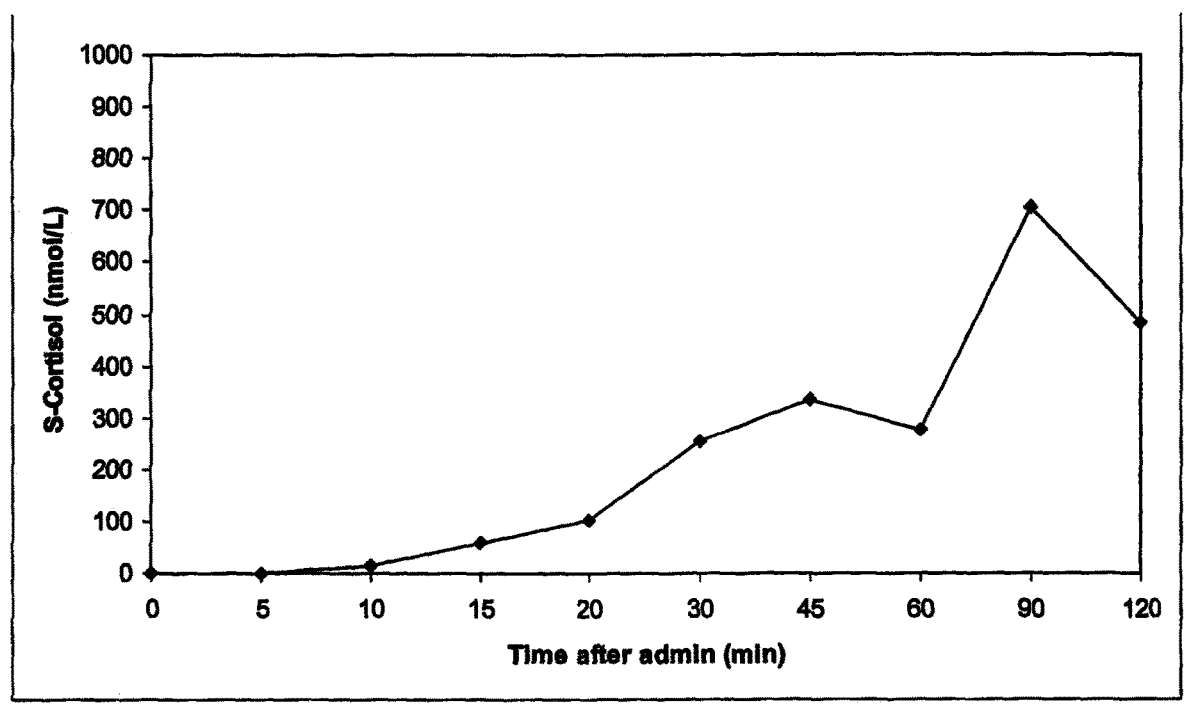
Figure 8:
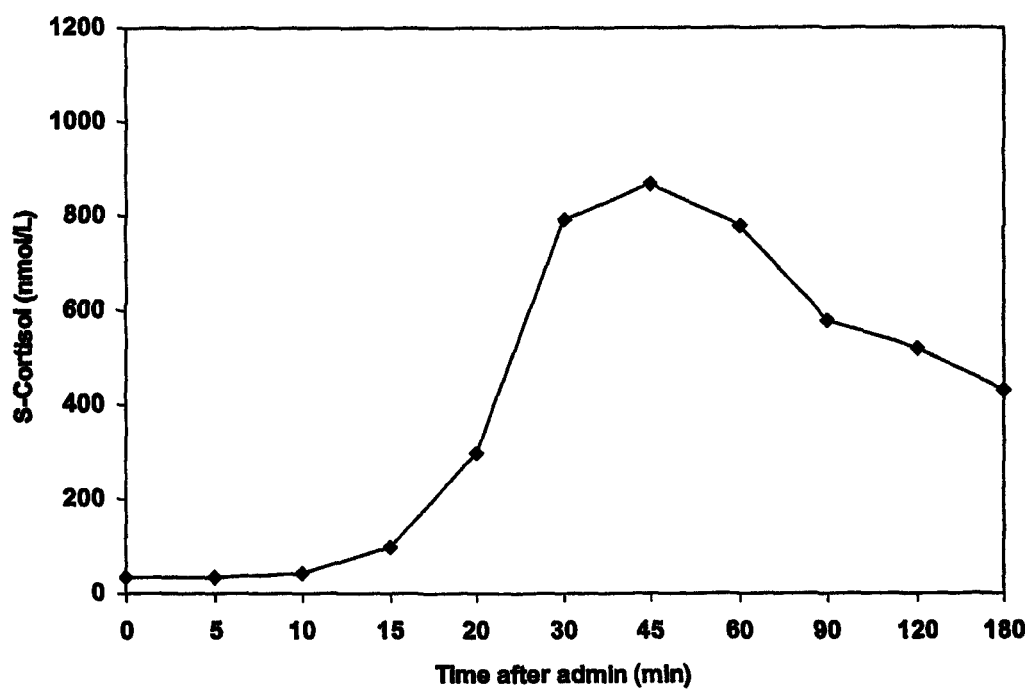

FIG. 4 shows results from Example 12. In vivo plasma profile. Extended release tablet, 7 mm diameter, medium compression force, 20 mg hydrocortisone, oral administration and solution of 10 mg hydrocortisone in 200 ml of water, oral administration. Subject has the endogenous glucocorticoid secretion suppressed by synthetic glucocorticoids FIG. 5 shows results from Example 18. The plasma concentration-time profile of cortisol following a single dose administration of composition A FIG. 6 shows results from Example 18. The plasma concentration-time profile of cortisol following a single dose administration of composition B FIG. 7 shows results from Example 18. The plasma concentration-time profile of cortisol following a single dose administration of composition C FIG. 8 shows results from Example 19. The plasma concentration-time profile of cortisol following a single dose administration of film A. Non-mucoadhesive thin-layer film, 6 cm$^2$, 10 mg hydrocortisone, buccal administration. Subject has the endogenous glucocorticoid secretion suppressed by synthetic glucocorticoids.

Figure 9:
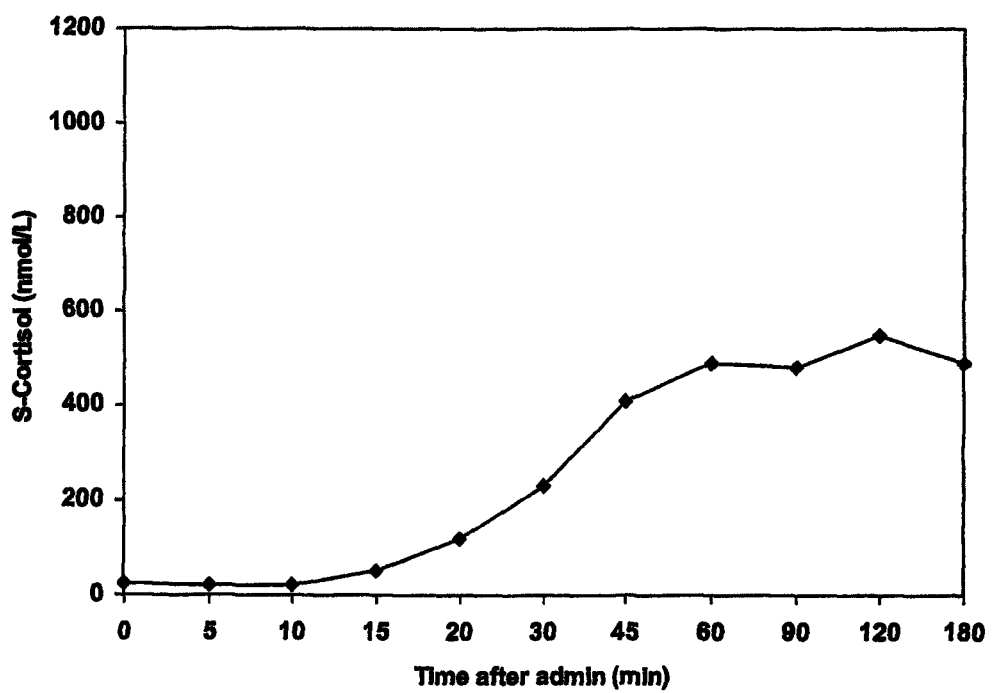

FIG. 9 shows results from Example 19. The plasma concentration-time profile of cortisol following a single dose administration of film B. Non-mucoadhesive thin-layer film, 6 cm$^2$, 11.2 mg hydrocortisone acetate, buccal administration. Subject has the endogenous glucocorticoid secretion suppressed by synthetic glucocorticoids.

Figure 10:
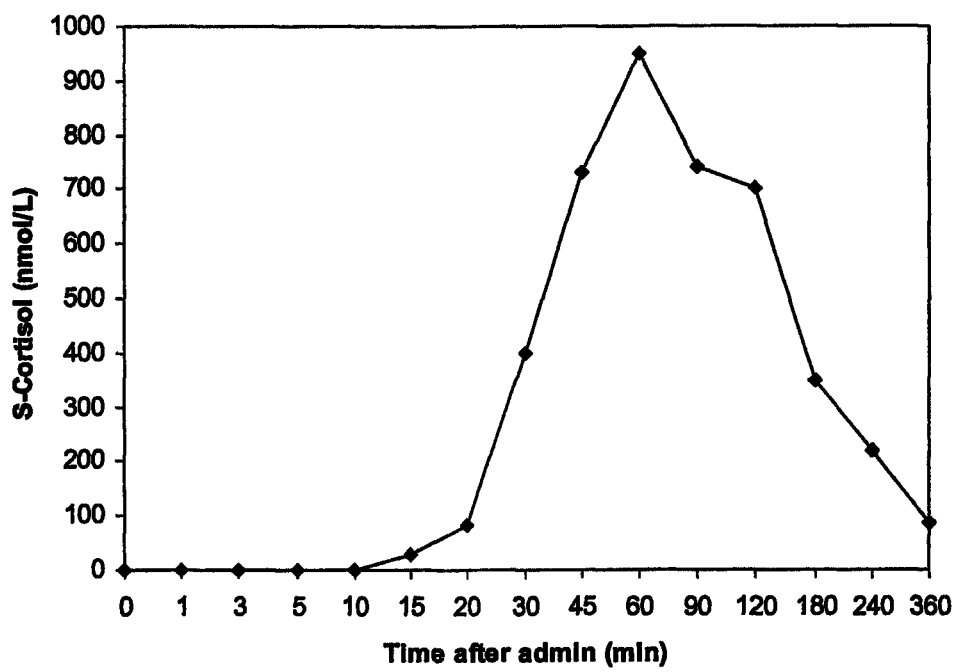
Figure 11:
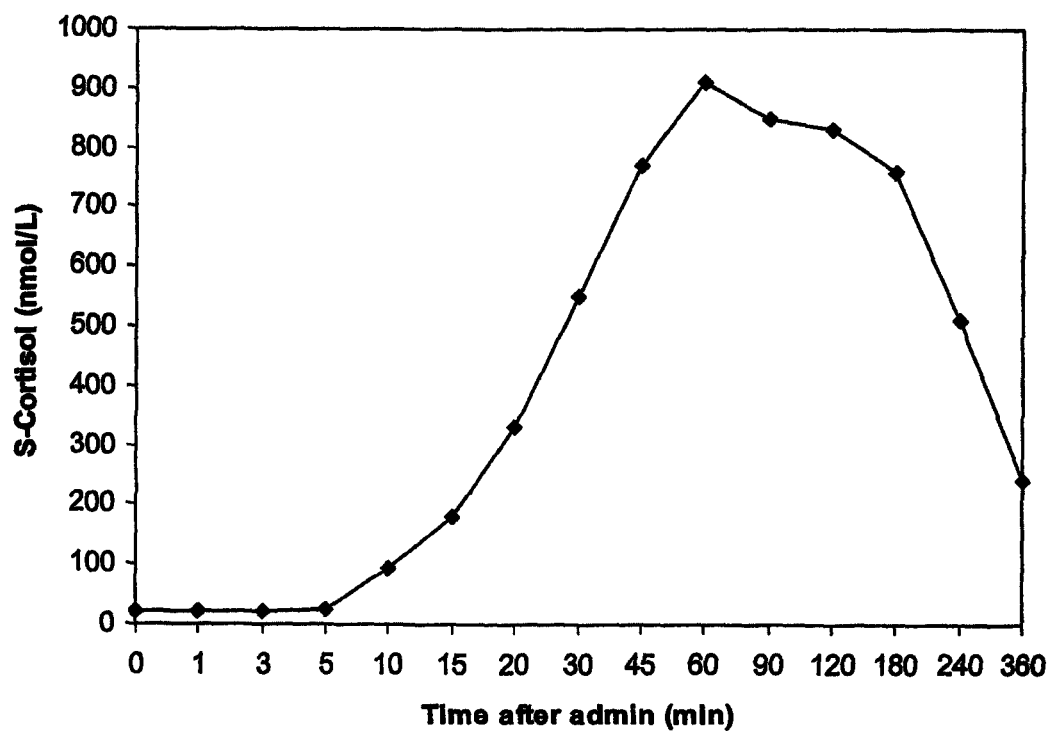
Figure 12:
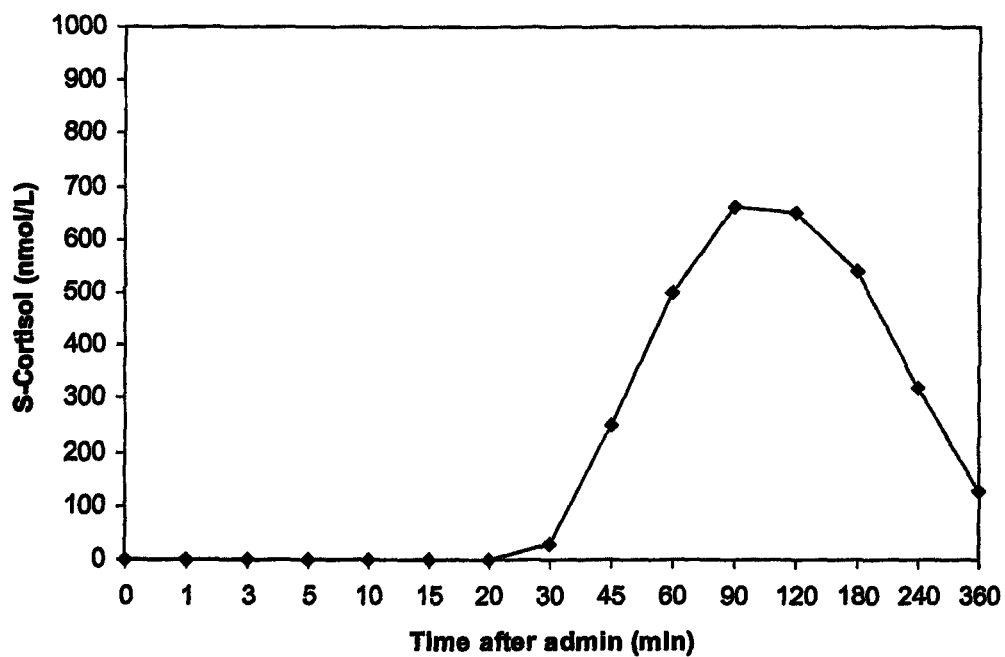
Figure 13:
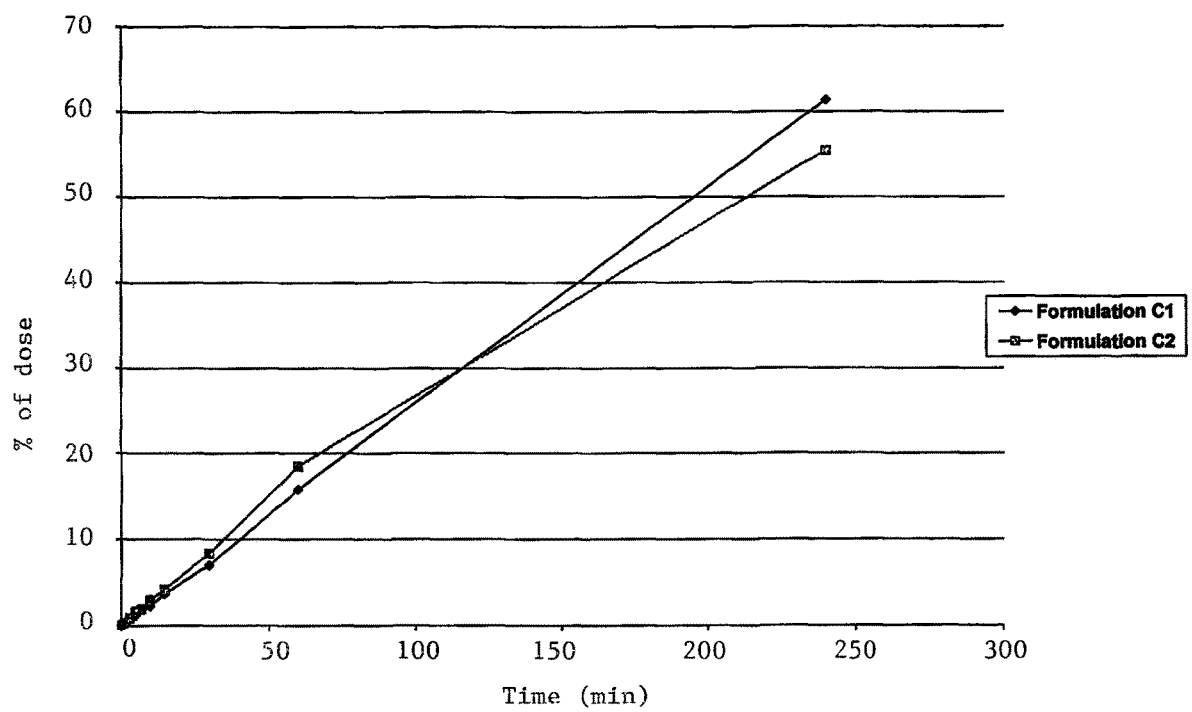

FIG. 10 shows results from Example 20. The plasma concentration-time profile of cortisol following a single dose administration of composition A. Muocadhesive thin-layer film, 10 mg hydrocortisone, buccal administration. Subject has the endogenous glucocorticoid secretion suppressed by synthetic glucocorticoids FIG. 11 shows results from Example 20. The plasma concentration-time profile of cortisol following a single dose administration of composition A. Mucoadhesive thin-layer film, 10 mg hydrocortisone, buccal administration. Subject has the endogenous glucocorticoid secretion suppressed by synthetic glucocorticoids FIG. 12 shows results from Example 21. The plasma concentration-time profile of cortisol following a single dose administration of-composition C. Mucoadhesive rapid-release tablet, 10 mg hydrocortisone, buccal administration. Subject has the endogenous glucocorticoid secretion suppressed by synthetic glucocorticoids FIG. 13 shows results from Example 22; dissolution curves of composition C from Example 21

Figure 14:
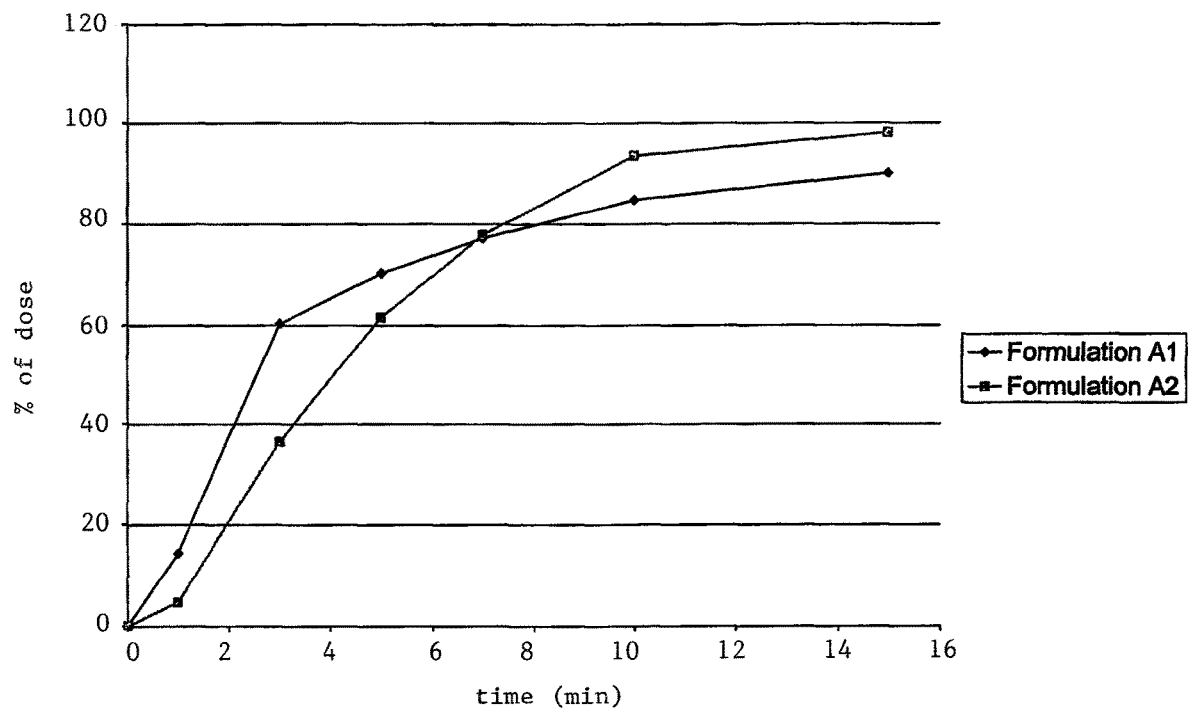

FIG. 14 shows results from Example 22; dissolution curves of composition A from Example 20

Figure 15:
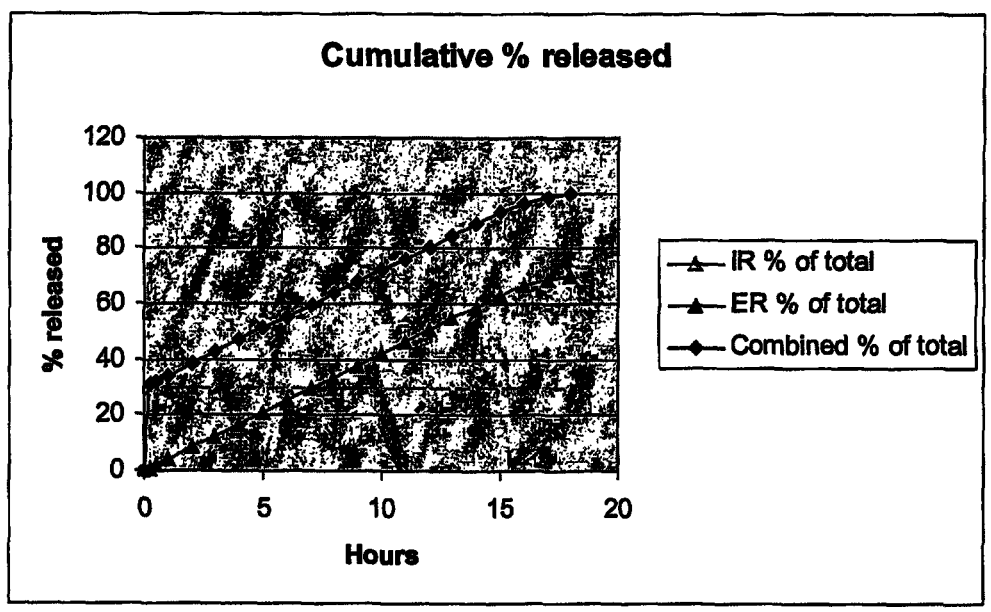

FIG. 15 shows a target in vitro release of hydrocortisone (HC) from a combined IR/ER product. IR part: 30% of total dose; ER part: 70% of total dose; IR part: Releases >90% within 20 minutes, target: 100% as fast as possible (within 15 minutes); ER part: 90% with constant rate during 14-16 hours (In this example 15 hours). The remaining 10% will be released at a lower rate. The cumulative release is shown.

Figure 16:
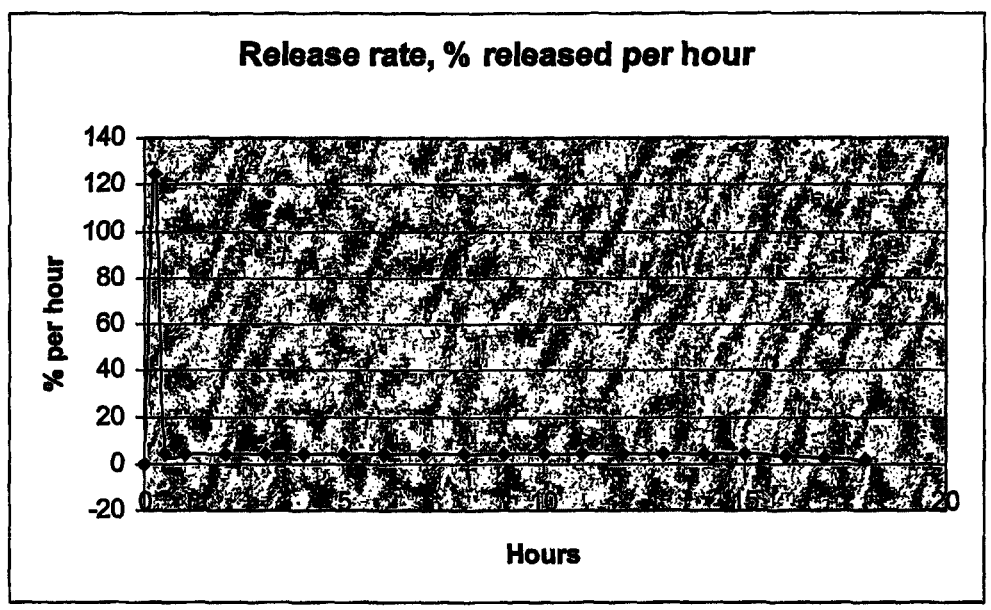

FIG. 16 shows the same release as in FIG. 15 but here given as release rate (% released per hour)

Figure 17:
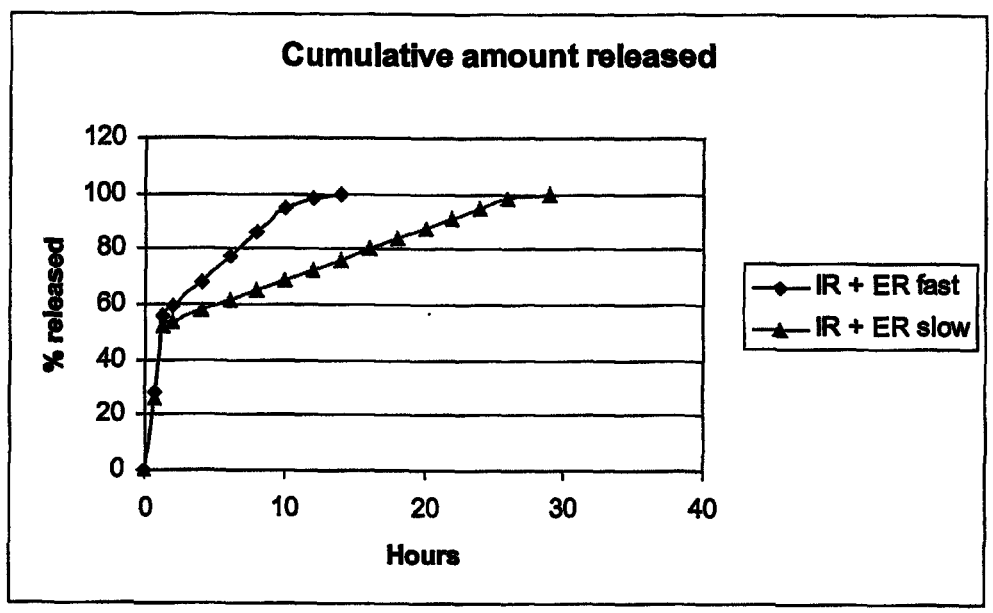

FIG. 17 shows a target in vitro release of hydrocortisone (HC) from a 15% IR and 85% ER combined IR/ER product; IR part: 15% of total dose with 50% released in 40 minutes. The rest is released within 75 minutes; ER part fast: 85% of total dose of which 90% is released during 10 hours (the rest at a lower rate); ER part slow: 85% of total dose of which 90% is released during 24 hours (the rest at a lower rate)

Figure 18:
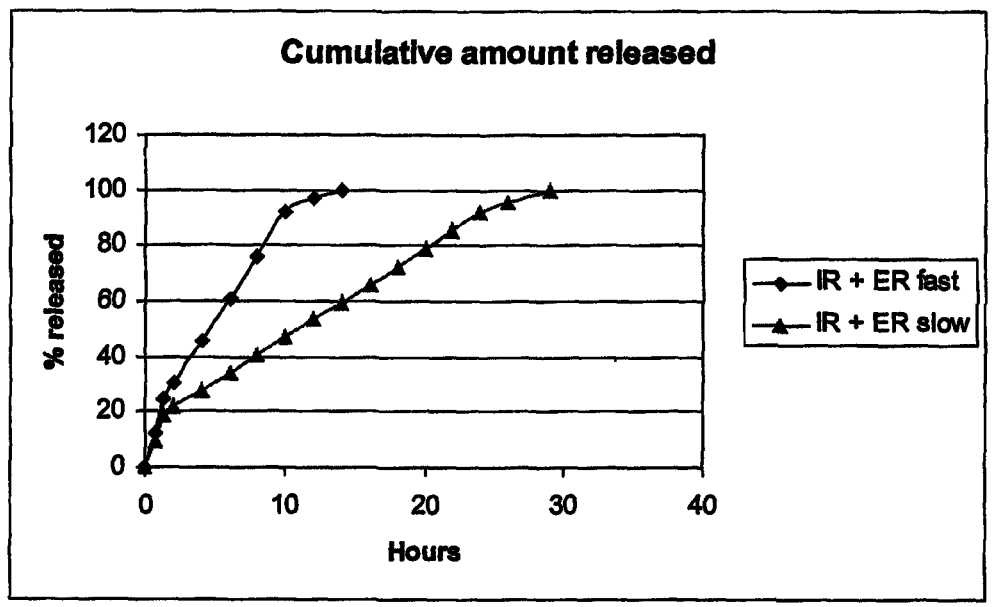

FIG. 18 shows a target in vitro release of hydrocortisone (HC) from a combined IR/ER product. IR part: 50% of total dose; ER part: 50% of total dose; IR part: 50% of total dose with 50% released in 40 minutes. The rest is released within 75 minutes; ER part fast: 50% of total dose of which 90% is released during 10 hours (the rest at a lower rate); ER part slow: 50% of total dose of which 90% is released during 24 hours (the rest at a lower rate)

FIGS. 19 and 20 are illustrations of different administration sites within the oral cavity The invention is further illustrated in the following non-limiting examples.

Materials

The materials used in the following examples were

| Trade name | Chemical substance | Manufacturer |
| --- | --- | --- |
| Acetone | USP/NF | |
| Betamethasone | USP/NF | |
| Calcium phosphate | USP/NF | |
| Carboxymetylcellulose | USP/NF | |
| Chitosan glutamate | USP/NF | |
| Crospovidone | USP/NF | |
| Ethylcellulose | USP/NF | |
| Hydrocortisone | Ph. Eur., Qual. D | Aventis, Switzerland (by Apoteksbolaget) |
| Hydrocortisone acetate | USP/NF | |
| Hydrocortisone 21-hemisuccinate sodium | Ph. Eur | Aventis, Switzerland (by Apoteksbolaget) |
| 2-OH-propyl-β-cyclodextrin | | |
| Hydroxypropylmethyl-cellulose | USP/NF | |
| Lactose | USP/NF | |
| Lactose anhydrous | USP/NF | |
| Levomenthol | USP/NF | |
| Magnesium stearate | Magnesium stearate | Kissei, Japan |
| Menthol | USP/NF | |
| Methocel E5 | Hydroxypropyl-methyl cellulose | Dow Chemicals, USA (by Colorcon) |
| Methocel ® KV 100 LV | USP/NF | Dow Chemicals, USA (by Colorcon) |
| Microcrystalline cellulose, Avicel ® PH-102 | USP/NF | FMC Corporation |
| Paraffin powder | USP/NF | |
| PEG 300 | USP/NF | |
| PEG 6000 | Polyethylene glycol | Svenska Hoechst AB |
| PEG 400 | Polyethylene glycol | Fluka, Switzerland |
| Prednisolone | USP/NF | |
| Polyox WSR 301 | Polyethylene oxide | Dow Chemicals, USA |
| Silicon dioxide, colloidal | USP/NF | |
| Sodium aluminium silicate | USP/NF | |
| Sodium dihydrogen phosphate | $NaH_2PO_4 \cdot 2\ H_2O$ | |
| Sodium stearyl fumarate | USP/NF | |
| Sorbitol | USP/NF | |
| Starch 1500 ®, Colorcon UK | Pre-gelatinised starch | Colorcon UK |
| Sugar | USP/NF | |
| Sugar/starch seeds | USP/NF | |
| Talc | USP/NF | |
| Triethyl citrate | USP/NF | |
| Xylitab 300 | | Xyrofin Kotka, Finland |
| Xylisorb 300 | | (Danisco Sweeteners Ltd, UK |
| Xylitol | USP/NF | Roquette, France |

Methods

The in vivo experiments reported herein were carried out on healthy volunteers. At 6 pm and 11 pm the day before administration of the test composition, the endogenous cortisol secretion was suppressed by oral administration of 2 mg of betamethasone.

The test composition was administered to healthy volunteers. The volunteers were in fasted state and were not allowed to take any food until noon. In the case a tablet is administered, it is ingested together with 200 ml of water. The test composition is administered between 8 am and 10 am on the day following the suppression of endogenous glucocorticoid secretion.

EXAMPLES

Example 1

Porous Matrix Tablet Releasing the Glucocorticoid by Diffusion

The following example relates to a porous matrix from which the glucocorticoid is released by diffusion. The matrix is coated with a film containing a readily water-soluble glucocorticoid for immediate release.

| Hydrocortisone | 20 g |
| --- | --- |
| Lactose | 30 g |
| Paraffin powder | 20 g |
| Sodium aluminium silicate | 20 g | is dry mixed and granulated with a 5% ethanol solution of ethyl cellulose

The wet mass is forced through a sieve, dried, milled and mixed with

| Calcium phosphate | 40 g |
| --- | --- | and finally with

| Magnesium stearate | 3 g |
| --- | --- |

The mixture is compressed into tablets containing 20 mg of hydrocortisone using 7 mm round concave punches. Approximate tablet weight 140 mg.

The tablets are coated with a water suspension containing

| Hydrocortisone 21-hemisuccinate sodium | 10% |
| --- | --- |
| Hydroxypropyl methylcellulose | 3% |
| Talc | 10% | until the coating on each tablet contains 6.7 mg of hydrocortisone 21-hemisuccinate sodium.

Example 2

Tablet Coated with a Water-Insoluble Film Containing a Pore-Forming Substance

The following example relates to a tablet that is coated with a water-insoluble film containing a pore-forming substance. The tablet is further coated with a water-soluble film containing the part of the glucocorticoid for immediate release.

| | |
|---|---|
| Hydrocortisone 21-hemisuccinate sodium | 20 g |
| Calcium phosphate | 75 g |
| Talc | 5 g |
| Magnesium stearate | 2 g | are dry mixed and compressed into tablets containing 20.1 mg of hydrocortisone 21-hemisuccinate sodium using 6 mm round concave punches with bevelled edges. Approximate tablet weight 103 mg.

The tablets are coated with an acetone suspension of

| | |
|---|---|
| Ethyl cellulose | 5% |
| Sugar micronized to a particle size < 10 μm | 10% | until each tablet carries a coating of about 40 mg.

The tablets are further coated with a water suspension containing

| | |
|---|---|
| Hydrocortisone 21-hemisuccinate sodium | 10% |
| Hydroxypropyl methylcellulose, 6 cps | 3% |
| Talc | 10% | until the outer coating on each tablet contains 6.7 mg of hydrocortisone 21-hemisuccinate sodium.

Example 3

Hydrophilic Matrix Tablet

This example relates to a hydrophilic gel matrix tablet that is dry coated with a coating containing the part of the glucocorticoid for immediate release.

| | |
|---|---|
| Hydrocortisone | 20 g |
| Sodium aluminium silicate | 15 g |
| Hydroxypropyl methylcellulose, 60 cps | 80 g | are mixed and granulated with ethanol. The wet mass is forced through a sieve, dried and milled. To the dry mixture is added

| | |
|---|---|
| Talc | 5 g |
| Magnesium stearate | 2 g |

After mixing for about 2 minutes the mixture is compressed into extended release tablets using 7 mm round flat punches. Each tablet contains 20 mg of hydrocortisone and has an approximate tablet weight of 117 mg.

| | |
|---|---|
| Hydrocortisone | 10 g |
| Lactose | 40 g |
| Hydroxypropyl methylcellulose, 6 cps | 5 g | are dry mixed and then granulated with water. The wet mass is forced through a sieve, dried and milled. To the dry mass is added

| | |
|---|---|
| Polyvinylpyrrolidone cross-linked | 5 g |

After mixing is added

| | |
|---|---|
| Magnesium stearate | 1 g | and mixing is continued during another 2 minutes.

Dry coated tablets are made by compressing about 61 mg of the tablet mass above around each extended release tablet using a Manesty DryCota™ tableting machine equipped with 9 mm round concave punches. The press-coated layer contains 10 mg of hydrocortisone.

Example 4

Capsules Containing a Mixture of Pellets for Immediate (IR Pellets) and Extended Release (ER Pellets)

ER Pellets

| | |
|---|---|
| Sugar/starch seeds, diameter 0.25-0.35 mm | 1 kg | are first coated in a fluidised bed equipped with a Wurster column with an ethanol/acetone 40/60 solution of

| | |
|---|---|
| Ethyl cellulose 10 cps | 5% |
| Triethyl citrate | 0.4% | to a coating thickness of about 3 μm
and then further coated with an ethanol/acetone 40/60 solution of

| | |
|---|---|
| Hydrocortisone | 5% |
| Hydroxypropyl methylcellulose 6 cps | 1% | to a weight gain of approximately 25%.

Using the same equipment the pellets are further coated with an ethanol/acetone 40/60 solution of

| | |
|---|---|
| Ethyl cellulose 10 cps | 5% |
| Hydroxypropyl methylcellulose 6 cps | 1.5% |
| Triethyl citrate | 0.3% | to a coating thickness of 20 μm.
IR Pellets

| | |
|---|---|
| Sugar/starch seeds, diameter 0.25-0.35 mm | 1 kg | are coated in a fluidised bed equipped with a Wurster column with a water suspension containing

| | |
|---|---|
| Hydrocortisone 21-hemisuccinate sodium | 10% |
| Hydroxypropyl methylcellulose, 6 cps | 3% |
| Talc | 10% | to a weight gain of approximately 75%.

An amount of ER pellets containing 20 mg of hydrocortisone (approximately 140 mg) and an amount of IR pellets containing 13.4 mg of hydrocortisone 21-hemisuccinate sodium (approximately 70 mg) are filled into hard gelatine capsules size No 2 in a two-station capsule-filling machine.

Example 5

Two-Layered Tablets

This example relates to a two-layered tablet comprising a hydrophilic gel matrix tablet for extended release on which a further layer is compressed containing the part of the glucocorticoid for immediate release.

| | |
|---|---|
| Hydrocortisone | 20 g |
| Sodium aluminium silicate | 15 g |
| Hydroxypropyl methylcellulose, 60 cps | 80 g | is granulated with ethanol. The wet mass is forced through a sieve, dried and milled.

To the dry mixture is added

| | |
|---|---|
| Talc | 5 g |
| Magnesium stearate | 2 g |

After mixing for about 2 minutes the mixture is at a low compression force compressed into about 117 mg tablets using 8 mm round flat punches in the first station of a two-station tabletting machine. Each tablet contains 20 mg of hydrocortisone.

| | |
|---|---|
| Hydrocortisone | 10 g |
| Lactose | 40 g |
| Hydroxypropyl methylcellulose, 6 cps | 5 g | are dry mixed and then granulated with water. The wet mass is forced through a sieve, dried and milled.

To the dry mass is added

| | |
|---|---|
| Polyvinylpyrollidone cross-linked | 5 g |

After mixing is added

| | |
|---|---|
| Magnesium stearate | 1 g | and mixing is continued during another 2 minutes.

Two-layer tablets are made by filling about 61 mg (containing 10 mg of hydrocortisone) of the tablet mass on top of the loosely compressed tablets above in the second station of the tabletting machine.

Example 6

ER Tablets

| | Mg per tablet |
|---|---|
| Hydrocortisone | 20 |
| Methocel ® KV 100 LV | 64 |
| Microcrystalline cellulose, Avicel ® PH-102 | 98 |
| Starch 1500 ®, Colorcon UK | 16 |
| Silicon dioxide, colloidal | 1 |
| Magnesium stearate | 1 |

All materials, except for magnesium stearate, were dry mixed until homogeneous. Magnesium stearate was added and mixing was continued during another two minutes. The powder blend was compressed into 200 mg tablets using 8 mm round concave punches. The tablets had a mean tablet height of 4.25 mm and a mean crushing strength of 10.8 kp. The average content of hydrocortisone was 19.3 mg per tablet.

The tablets were analysed with respect to dissolution rate using USP Dissolution Apparatus No 2, paddle, with 500 ml simulated intestinal fluid without enzymes and a stirring rate of 50 rpm. Samples were withdrawn at different times and analysed for hydrocortisone by HPLC. The median results for three individually analysed tablets were:

| | Time | | | | | | | |
|---|---|---|---|---|---|---|---|---|
| | 1 h | 3 h | 5 h | 7 h | 9 h | 11 h | 13 h | 15 h |
| % dissolved | 7 | 24 | 41 | 58 | 70 | 83 | 90 | 95 |

The extended release tablets were tested in human volunteers. FIG. 1 shows the results obtained.

In a fluidised bed equipped with a Wurster column the ER tablets are coated with a water suspension containing

| | |
|---|---|
| Hydrocortisone | 2% |
| Hydroxypropyl methylcellulose | 0.7% |
| Talc | 2% | until the coating on each tablet contains 7 mg of hydrocortisone.

The coating is rapidly dissolving and dissolution is complete within 15 minutes.

The cumulative dissolution of hydrocortisone of the coated tablets is shown in FIG. 2.

Example 7

Kit Containing an Immediate Release (IR) Tablet and an Extended Release (ER) Tablet IR tablets for oral or sublingual use:

| | Mg per tablet |
|---|---|
| Betamethasone | 0.4 |
| Xylitab ®300[a] | 40 |
| Lactose anhydrous USP/NF | 5 |
| Microcrystalline cellulose USP/NF | 10 |
| Crospovidone USP/NF | 4 |

|                        | Mg per tablet |
|------------------------|---------------|
| Sodium stearyl fumarate | 1            |
| Water                  | qs            |

[a] Direct compression xylitol from Danisco Sweeteners Ltd UK

Dry mix lactose and microcrystalline cellulose. Dissolve betamethasone in a small amount of water and disperse the solution over the powder blend. Mix and dry. Add Xylitab and crospovidone and dry mix until the blend is homogeneous. Add sodium stearyl fumarate and continue blending for another 2 minutes. Compress the blend to tablets in a tablet press using 6 mm round concave punches.

ER Tablets:

|                              | Mg per tablet |
|------------------------------|---------------|
| Betamethasone                | 0.8           |
| Methocel K100 Premium LV CR[b] | 65          |
| Microcrystalline cellulose USP/NF | 70       |
| Colloidal silicon dioxide    | 1             |
| Magnesium stearate           | 1             |

[b] Dow Chemical Company

Blend all materials, except for magnesium stearate, until homogeneous in a suitable mixer. Then add magnesium stearate and blend for another 2 minutes. Compress to tablets in a tablet press equipped with 7.5 mm round concave punches.

Package one IR tablet and one ER tablet in a suitably designed package to obtain a kit.

Example 8

Kit Containing an Immediate Release (IR) Film and an Extended Release (ER) Tablet Thin films for administration to the oral cavity:

|                        | % by weight |
|------------------------|-------------|
| Prednisolone           | 0.75        |
| PEG 400 USP/NF         | 2           |
| Methocel E5, Dow Chemical | 4        |
| Xylitol, Roquette France | 1         |
| Water                  | up to 100   |

Methocel was added to approximately 90% of the total amount of distilled water and stirred with a magnetic stirrer until Methocel was completely dissolved. PEG 400 was added under continued stirring, followed by xylitol and prednisolone. Water was added to final weight and stirring was continued during four hours.

330 µl of the solution was pipetted into 16 mm diameter flat-bottomed PVC blisters. The solutions were allowed to dry at room temperature over night and the blister packs were sealed with heat-seal lacquered aluminium foil.

ER Tablets:

|                              | Mg per tablet |
|------------------------------|---------------|
| Prednisolone                 | 1.5           |
| Methocel K100 Premium LV CR[b] | 65          |
| Microcrystalline cellulose USP/NF | 70       |

|                           | Mg per tablet |
|---------------------------|---------------|
| Colloidal silicon dioxide | 1             |
| Magnesium stearate        | 1             |

[b] Dow Chemical Company

Blend all materials, except for magnesium stearate, until homogeneous in a suitable mixer. Then add magnesium stearate and blend for another 2 minutes. Compress to tablets in a tablet press equipped with 7.5 mm round concave punches.

Package one IR film blister and one ER tablet to obtain a suitably designed kit.

Example 9

Kit Containing an Immediate Release (IR) Oral Solution and an Extended Release (ER) Tablet Oral Solution:

|                      |           |
|----------------------|-----------|
| Prednisolone acetate | 0.9 mg    |
| Sorbitol             | 60 mg     |
| Menthol              | 1.2 mg    |
| Sterile water        | 5 ml      |

Make a solution and fill into a moisture tight aluminium foliated sachet.

Package one sachet and one ER tablet to obtain a suitably designed kit.

Example 10

Kit Containing an Immediate Release (IR) Sublingual Spray and an Extended Release (ER) Tablet Sublingual Spray of Hydrocortisone:

|                              | mg/ml        |
|------------------------------|--------------|
| Hydrocortisone acetate       | 10           |
| Carboxymetylcellulose        | 0.8 (0.08%)  |
| 2-OH-propyl-β-cyclodextrin   | 40           |
| PEG 300                      | 5            |
| Menthol                      | 0.3          |
| Sorbitol                     | 12           |
| Levomenthol                  | 2.0          |
| $NaH_2PO_4 \cdot 2H_2O$      | 2            |
| Water                        | qs           |

Dissolve hydrocortisone acetate in a small amount of water. Mix with 2-OH-propyl-β-cyclodextrin, let stand for 1 hour. Add carboxymethylcellulose and mix. Add PEG 300, menthol, sorbitol, levomenthol and $NaH_2PO_4 \cdot 2\ H_2O$. Add water up to final volume. Dispense into a spray package that delivers 0.58 ml per dose (5 mg of hydrocortisone).

Hydrocortisone ER Tablets

|                                       | Mg per tablet |
|---------------------------------------|---------------|
| Hydrocortisone                        | 10            |
| Methocel® KV 100 LV                   | 64            |
| Microcrystalline cellulose, Avicel® PH-102 | 98       |
| Starch 1500®, Colorcon UK             | 16            |

-continued

| | Mg per tablet |
|---|---|
| Silicon dioxide, colloidal | 1 |
| Magnesium stearate | 1 |

Dry mix all materials, except for magnesium stearate, until homogeneous. Add magnesium stearate and continue mixing another two minutes. Compress the powder blend into 200 mg tablets using 8 mm round concave punches.

Dispense the sublingual spray and ER tablets into suitably designed kit(s).

Example 11

Kit Containing an Immediate Release Film and an Extended Release Tablet

A kit is provided containing i) an immediate release film containing 10 mg hydrocortisone and prepared as described in example 20 composition A and ii) an extended release tablet containing 20 mg hydrocortisone and prepared according to Example 6. The component i) is administered buccally and the component ii), i.e. the tablet is ingested together with 200 ml of water. The two components are taken simultaneously. The results are shown in FIG. 3.

Example 12

Kit Containing an Oral Solution of Hydrocortisone for Immediate Release and an Extended Release Tablet An oral solution is prepared by dissolving 10 mg of hydrocortisone in 200 ml of water and the extended release tablet corresponds to that of Example 6. The two compositions are given to human volunteers simultaneously and the results are shown in FIG. 4.

In the following are described examples of immediate release compositions. Each of the exemplified compositions can be used as an immediate release component in a kit according to the invention. The extended release component may be any suitable glucocorticoid-containing composition releasing the glucocorticoid in an extended manner as defined herein.

Example 13

Betamethasone IR Tablet for Peroral or Buccal Administration

| | Mg per tablet |
|---|---|
| Betamethasone | 0.4 |
| Xylitab®300[a] | 45 |
| Microcrystalline cellulose NF | 10 |
| Crospovidone NF | 4 |
| Water | qs |
| Sodium stearyl fumarate NF | 1 |

[a] Direct compression xylitol from Danisco Sweeteners Ltd, UK

Dissolve betamethasone in a small amount of water.
Disperse the solution over the microcrystalline cellulose. Mix and dry.
Add Xylitab and crospovidone and dry mix in a suitable mixer until a homogeneous blend is achieved.

Then add sodium stearyl fumarate and continue mixing another two minutes. Compress the powder blend in a suitable tablet press using 6 mm round concave punches.

Example 14

Sublingual Spray of Betamethasone

| | mg/ml |
|---|---|
| Betamethasone | 0.4 |
| Carboxymetylcellulose | 0.8 (0.08%) |
| PEG 300 | 5 |
| Menthol | 0.3 |
| Sorbitol | 12 |
| Levomenthol | 2.0 |
| $NaH_2PO_4*2H_2O$ | 2 |
| Water | qs |

Dissolve betamethasone in a small amount of water. Add carboxymetylcellulose and mix. Add PEG 300, menthol, sorbitol, levomenthol and $NaH_2PO_4*2\ H_2O$. Add water up to final volume.

Example 15

Sublingual Spray of Betamethasone

| | mg/ml |
|---|---|
| Betamethasone | 0.4 |
| Chitosan glutamate | 10 |
| Menthol | 0.1 |
| Levomenthol | 1.5 |
| $NaH_2PO_4*2H_2O$ | 2 |
| Water | qs |

Dissolve betamethasone in a small amount of water. Add chitosan glutamate and mix. Filter through 0.2 µm membrane filter. Add menthol, levomenthol and $NaH_2PO_4*2\ H_2O$. Add water up to final volume.

Example 16

Sublingual Spray of Hydrocortisone

| | |
|---|---|
| Hydrocortisone acetate | 10 |
| Carboxymetylcellulose | 0.8 (0.08%) |
| 2-OH-propyl-β-cyclodextrin | 40 |
| PEG 300 | 5 |
| Menthol | 0.3 |
| Sorbitol | 12 |
| Levomenthol | 2.0 |
| $NaH_2PO_4*2H_2O$ | 2 |
| Water | qs |

Dissolve hydrocortisone in a small amount of water. Mix with 2-OH-propyl-β-cyclodextrin, let stand for 1 hour. Add carboxymethylcellulose and mix. Add PEG 300, menthol, sorbitol, levomenthol and $NaH_2PO_4*2\ H_2O$. Add water up to final volume.

Example 17

Sublingual Spray of Hydrocortisone

|  | mg/ml |
| --- | --- |
| Hydrocortisone acetate | 10 |
| Chitosan glutamate | 10 |
| 2-OH-propyl-β-cyclodextrin | 40 |
| Menthol | 0.1 |
| Levomenthol | 1.5 |
| $NaH_2PO_4 \cdot 2H_2O$ | 2 |
| Water | qs |

Dissolve hydrocortisone in a small amount of water. Mix with 2—OH-propyl-β-cyclodextrin, let stand for 1 hour. Add chitosan glutamate and mix. Filter through 0.2 µm membrane filter. Add menthol, levomenthol and $NaH_2PO_4 \cdot 2H_2O$. Add water up to final volume.

Example 18

Thin-layer Film of Hydrocortisone

Composition A:

|  | % w/w |
| --- | --- |
| Hydrocortisone | 3% |
| Na-alginate PH157 | 2% |
| Water | 95% |

Composition B:

| Hydrocortisone acetate | 3.4% |
| --- | --- |
| Na-alginate PH157 | 2% |
| Water | 94.6% |

Composition C:

| Hydrocortisone | 3% |
| --- | --- |
| Metolose 60SH-50 | 2% |
| Water | 95% |

The films were made as described in the following:
1. Amount polymer, glucocorticoid and $H_2O$ were weighed.
2. The glucocorticoid was added to the water during stirring.
3. The formulation was kept on stirring until a suspension was obtained.
4. The polymer was added to the suspension.
5. The formulation was kept on stirring until a uniform gel was obtained (minimum 2 h).
6. 0.5 g gel was weighed in empty blisters and placed in a heating cupboard (Drying: 25° C. for 22 h).

Table. In vitro dissolution (rotating basket 100 rpm, phosphate buffer pH=7.0, one unit per 500 ml medium) after 1, 3, 5, 10 and 15 min as a percentage of 10 mg hydrocortisone. Units with 10 mg hydrocortisone in polymers of sodium alginate (Na-alg), hypromeilose (HPMC) and approx. 7 mg/unit. Two units were tested with Na-alg and HPMC. The mean value is tabulated. The results in the following table reflect the rank order regarding viscosity, i.e. HPMC has the lowest viscosity and Na-aig the highest.

| Composition | Polymer | 1 min, % | 3 min, % | 5 min, % | 10 min, % | 15 min, % |
| --- | --- | --- | --- | --- | --- | --- |
| A | Na-alg | 15 | 25 | 38 | 65 | 84 |
| B | Na-alg | 15 | 25 | 38 | 65 | 84 |
| C | HPMC | 18 | 48 | 67 | 88 | 92 |

In vivo plasma profiles in humans, N=1 per composition
Dexamethasone suppression test, fasting state, otherwise as described in the paragraph denoted "Method".

The results show (FIGS. 5-7) that the use of hydrocortisone acetate does not seem to be suitable for an immediate release composition. This was further investigated in the following example.

Example 19

Non-Mucoadhesive Immediate Release Films

Two films were prepared essentially similar to Example 20—composition A. Film A contains 10 mg of hydrocortisone and film B contains 11.2 mg of hydrocortisone acetate. The results from in vivo testing after buccal administration are shown in FIGS. 8 and 9. The results show that even if the films are not bioadhesive, a fast onset of the absorption into the systemic circulation after single dose administration of Film A is obtained. In contrast, the results obtained with the film containing hydrocortisone acetate indicate that this compound does not seem to be suitable when a fast onset of the absorption into the systemic circulation of the glucocorticoid is required.

Example 20

Thin-Layer Films for Immediate Release or Extended Release

Batches of glucocorticoid films were prepared from the following compositions A and B:

| Rapid-release composition A: | |
| --- | --- |
| Component | % w/w |
| PEG 400 | 2.0 |
| Hydrocortisone | 3.0 |
| Methocel E5 | 4.0 |
| Xylitol | 1.0 |
| Water | 90 |

| Slower release composition B: | |
| --- | --- |
| Component | w/w % |
| PEG 400 | 1.3 |
| Hydrocortisone | 3.0 |
| Methocel E5 | 5.7 |
| Water | 90 |

To distilled water (18 ml) in 50 ml round-bottomed glass flask provided with a magnetic stirred was added Methocel E5. After the Methocel had dissolved completely PEG 400 was added under continued stirring, followed by xylitol (Composition A only) and hydrocortisone. Stirring was continued for 4 h.

Into flat-bottomed PVC-blisters (Inpack AB, Lund, Sweden) 16 mm in diameter was pipetted (Finnpipette; automatic) 330 μl of solution A or B into each blister trough. The solutions were allowed to dry at Mom temperature over night. The next day 10 films were removed for dose analysis. Each film was dissolved in 100 ml of water/ethanol (95%) 9:1 (w/w). The solutions were analysed by UV spectroscopy at 242 nm. Mean contents of 10.19 mg and 9.83 mg hydrocortisone per blister (SD 0.29 and 0.14, respectively) were found for Compositions A and B, respectively.

The hydrocortisone compositions were tested in two human subjects after labial administration. The subjects had their endogenous glucocorticoid secretion suppressed by synthetic glucocorticoids. The plasma concentration of cortisol was monitored during 360 min after the labial administration, and the serum concentration time profiles from these two different subjects are shown in FIGS. 10 and 11.

It is clearly seen that the rate and extent of mucosal uptake of hydrocortisone is high and the appearance of cortisol in serum is rapid, as the first measured plasma concentration was attained already at 10-15 min.

These serum pharmacokinetic data illustrate that a formulation of the invention for oral mucosa administration results in a high rate and extent of mucosal absorption of the active drug, even though a small volume of fluid is available for dissolution at the site of administration and absorption in this route of drug delivery.

Example 21

Glucocorticoid Tablets for Immediate or Extended Release

Glucocorticoid tablets were manufactured by direct compression of the dry-mixed powderous components to the following compositions C and D:

| Component | Per Batch |
| --- | --- |
| Rapid-release composition C: | |
| PEG 6000 | 8.7 g |
| Hydrocortisone | 2.5 g |
| Xylitab 300 | 8.7 g |
| Mg stearate | 0.16 g |
| Slow-release composition D: | |
| PEG 6000 | 6.94 g |
| Hydrocortisone | 2.5 g |
| Xylisorb | 6.94 g |
| Polyox WSR 301 | 3.46 g |
| Mg stearate | 0.16 g |

Batch Size 100 Tablets

The powderous components were sieved (mesh size 0.7 mm) and dry-mixed by shaking by hand in a small tin can for five min. The homogeneity of the mixture was analyzed by the same method as used for analysis of the tablets. Tabletting was carried out with a DIAF tabletting machine using a flat circular punch 7 mm in diameter (with a dividing score). The hydrocortisone dose in 10 tablets was assessed by the same method as used for the films. Mean contents of 9.53 mg and 9.72 mg hydrocortisone per tablet (SD 0.15 and 0.14, respectively) were found for compositions C and D, respectively.

Tablet thickness (10 tablets): 1.72-1.78 mm (C); 1.79-1.84 mm (D).

Friability (20 tablets): 0.6% (C); 0.4% (D).

Tablet hardness (10 tablets): 23.7 N(C); 22.9 N (D).

The compositions were tested after oral administration to two human subjects (FIG. 12).

The rate of absorption of the active substance into the systemic circulation from the solid dosage forms of Example 21 was somewhat slower than that of compositions from Example 20, which means that it is possible to adjust the absorption rate of hydrocortisone into the systemic circulation by introducing changes in the composition and function of the labial pharmaceutical formulation.

Example 22

In Vitro Dissolution Profile

The in vitro dissolution profiles of hydrocortisone from drug formulations according to Example 20 and 21 were followed over time in a standardized controlled in vitro environment. A United States Pharmacopoeia dissolution apparatus II (paddle) coupled to automatic sampling devices and software was used for acquiring release profiles of the drug formulations in a neutral pH environment. The dissolution profile was acquired at 37° C., 50 rpm of the paddles, in a total of 300 ml of water. Sampling was performed at 0, 1, 3, 5, 7, 10 and 15 minutes following the insertion of the pharmaceutical composition in the example in the dissolution medium.

The dissolution profile from each formulation was monitored in two experiments up to 360 min after administration, and the corresponding dissolution time profiles are shown in FIGS. 13 and 14, respectively. The release rate is given as the percent of dose over time.

The release rate from the solid dosage forms of Example 21 was somewhat slower (FIG. 14). This means that it is possible to adjust the release rate of hydrocortisone by introducing changes in the composition and function of the oronasopharyngeal pharmaceutical preparation.

The invention claimed is:

1. A method for once daily treatment of a glucocorticoid deficiency disorder in a patient in need thereof, comprising administering to said patient a therapeutically effective amount of a coated tablet dosage form once daily in the morning, said coated tablet dosage form comprising:

(a) an extended release tablet core and an immediate release coating surrounding said extended release tablet core; and (b) a total dose of about 1 mg to about 80 mg of hydrocortisone;

wherein said extended release tablet core comprises hydrocortisone, the amount of hydrocortisone present in said extended release tablet core is about 60% to 80% of the total amount of hydrocortisone present in said coated tablet dosage form and is released over an extended period of time of at least 8 hours, wherein said immediate release coating comprises hydrocortisone and the amount of hydrocortisone present in said immediate release coating is about 20% to 40% of the total amount of hydrocortisone in said coated tablet dosage form.

2. The method according to claim 1, wherein a hydrocortisone serum level of at least about 200 nmol/l is obtained within 45 min after administration of said coated tablet dosage form to said patient.

3. The method according to claim 1, wherein a hydrocortisone serum level of at least about 200 nmol/l is obtained within 30 min after administration of said coated tablet dosage form to said patient.

4. The method according to claim 1, wherein a hydrocortisone serum level in a range of from about 400 to about 1000 nmol/l is obtained 2 hours after administration of said coated tablet dosage form to said patient.

5. The method according to claim 1, wherein a hydrocortisone serum level in a range from about 200 to about 600 nmol/l is obtained 6 hours after administration of said coated tablet dosage form to said patient.

6. The method according to claim 5, wherein the hydrocortisone serum level obtained is in a range of from about 200 to about 400 nmol/l.

7. The method according to claim 1, wherein a hydrocortisone serum level in a range of from about 50 to about 300 nmol/l is obtained 10 hours after administration of said coated tablet dosage form to said patient.

8. The method according to claim 1, wherein a hydrocortisone serum level in a range of from about 50 to about 200 nmol/l is obtained 14 hours after administration of said coated tablet dosage form to said patient.

9. The method according to claim 1, wherein the coated tablet dosage form is administered to said patient at wake-up in the morning between about 4 am and noon.

10. The method according to claim 9, wherein the coated tablet dosage form is administered to said patient in a fasted state.

11. The method according to claim 1, wherein a hydrocortisone serum level is obtained, in a time period corresponding to about 0.5 hours to about 7 hours after administration of the coated tablet dosage form to said patient, which substantially mimics the serum level of cortisol of a healthy subject in the morning from 6 am to noon.

12. The method according to claim 1, wherein a 3 hour substantially hydrocortisone-free serum level is obtained within a time period from about 10 pm to about 6 am.

13. The method according to claim 1, wherein at least 50% of the hydrocortisone in the immediate release coating is released within the first 30 min of an in vitro dissolution test according to USP employing USP Dissolution Apparatus No. 2. (paddle); 50 rpm and simulated intestinal fluid without enzymes as dissolution medium.

14. The method according to claim 1, wherein the hydrocortisone of the extended release tablet core is released over an extended period of time of at least 10 hours as determined by an in vitro dissolution test according to USP employing USP Dissolution Apparatus No. 2. (paddle); 50 rpm and simulated intestinal fluid without enzymes as dissolution medium.

15. The method according to claim 1, wherein at least 50% of the total hydrocortisone in the coated tablet dosage form is released within 10 hours of an in vitro dissolution test according to USP employing USP Dissolution Apparatus No. 2. (paddle); 50 rpm and simulated intestinal fluid without enzymes as dissolution medium.

16. The method according to claim 1, wherein said glucocorticoid deficiency disorder is adrenal insufficiency.

17. The method according to claim 1, wherein said extended release tablet core further comprises one or more excipients selected from the group consisting of hydroxypropylmethylcellulose, microcrystalline cellulose, pregelatinized starch, colloidal silica, and magnesium stearate.

18. The method according to claim 1, wherein said immediate release coating further comprises one or more coating materials selected from the group consisting of hydroxypropylmethylcellulose, polyvinyl alcohol, polyethylene glycol, titanium dioxide and talc.

19. The method according to claim 1, wherein the coated tablet dosage form is for oral administration.

20. The method according to claim 1, wherein the coated tablet dosage form is administered to said patient at wake-up in the morning between about 6 am and 8 am.

21. The method according to claim 1, wherein the coated tablet dosage form contains about 5 mg to about 50 mg hydrocortisone.

22. The method according to claim 1, wherein the coated tablet dosage form contains 20 mg hydrocortisone.

23. The method according to claim 1, wherein the coated tablet dosage form contains 5 mg hydrocortisone.

* * * * *

UNITED STATES PATENT AND TRADEMARK OFFICE
CERTIFICATE OF CORRECTION

PATENT NO. : 10,583,146 B2
APPLICATION NO. : 14/255332
DATED : March 10, 2020
INVENTOR(S) : Stanko Skrtic et al.

It is certified that error appears in the above-identified patent and that said Letters Patent is hereby corrected as shown below:

On the Title Page

Left column under "Related U.S. Application Data (63)", please delete: "PCT/EP2005/000440" and insert -- "PCT/EP2005/004400" -- therefor.

Signed and Sealed this
Nineteenth Day of May, 2020

Andrei Iancu
*Director of the United States Patent and Trademark Office*